(12) United States Patent
Suda et al.

(10) Patent No.: US 7,855,300 B2
(45) Date of Patent: Dec. 21, 2010

(54) BIS(TRIMETHYLSILYL)PHENYL COMPOUND OR SALT THEREOF, AND USE THEREOF

(75) Inventors: Yoshimitsu Suda, Hanno (JP); Hiromi Oshiumi, Hanno (JP); Koji Murakami, Hanno (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/682,097

(22) PCT Filed: Oct. 10, 2008

(86) PCT No.: PCT/JP2008/068421

§ 371 (c)(1),
(2), (4) Date: Apr. 8, 2010

(87) PCT Pub. No.: WO2009/048123

PCT Pub. Date: Apr. 16, 2009

(65) Prior Publication Data

US 2010/0210591 A1    Aug. 19, 2010

(30) Foreign Application Priority Data

Oct. 11, 2007    (JP) .............................. 2007-265464

(51) Int. Cl.
    *C07F 7/10*    (2006.01)
(52) U.S. Cl. ....................... 556/422; 556/407
(58) Field of Classification Search ................. 556/422, 556/407
    See application file for complete search history.

(56) References Cited

U.S. PATENT DOCUMENTS 5,750,515 A    5/1998    Shibata et al.

FOREIGN PATENT DOCUMENTS

| JP | 02-247185 A | 10/1990 |
| JP | 2008-094727 A | 4/2008 |
| WO | 2009057199 A1 | 5/2009 |

OTHER PUBLICATIONS

Smith et al., "Retinoids in Cancer Therapy", Journal of Clinical Oncology, vol. 10, No. 5, May 1992, pp. 839-864.

Benedetti et al., "Retinoid-Induced Differentiation of Acute Promyelocytic Leukemia Involves PML-RARα-Mediated Increase of Type II Transglutaminase", Blood, vol. 87, No. 5, Mar. 1, 1996, pp. 1939-1950.

Mendelsohn et al., "Developmental analysis of the retinoic acid-inducible RAR-β2 promoter in transgenic animals", Development 113, pp. 723-734, 1991.

Look et al, "Marked resistance of RARγ-deficient mice to the toxic effects of retinoic acid", Am. J. Physiol., Jul. 1995, 269, pp. E91-E98.

Rizvi et al., "Initial Clinical Trial of Oral TAC-101, a Novel Retinoic Acid Receptor-Alpha Selective Retinoid, in Patients with Advanced Cancer", Journal of Clinical Oncology, vol. 20, No. 16, Aug. 15, 2002, pp. 3522-3532.

*Primary Examiner*—Elvis O Price
(74) *Attorney, Agent, or Firm*—Rothwell, Figg, Ernst & Manbeck, P.C.

(57) ABSTRACT

The present invention provides a compound that exhibits an excellent antitumor effect and reduces side effects, such as skin disorders, of the existing retinoid by selectively activating on the nuclear receptor RARα, thereby possibly producing significant improvement of clinical profits. Specifically, the present invention provides a bis(trimethylsilyl)phenyl compound represented by Formula (I):

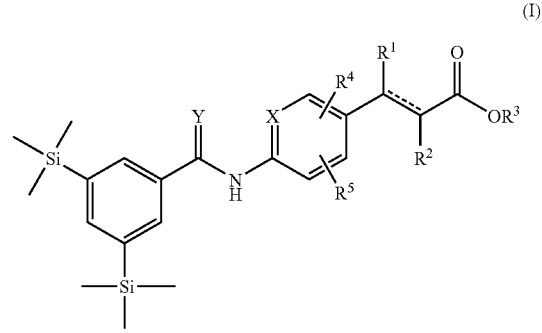

wherein X is N or CH; Y is O or S; R1, R2, and R3 are the same or different and are hydrogen or lower alkyl; R4 and R5 are the same or different and are hydrogen, lower alkyl, or halogen; and a bond between a carbon atom to which R1 is attached and a carbon atom to which R2 is attached is a single bond or a double bond;
or a salt thereof.

11 Claims, 2 Drawing Sheets

: p<0.01, *: p<0.001

BIS(TRIMETHYLSILYL)PHENYL COMPOUND OR SALT THEREOF, AND USE THEREOF

CROSS REFERENCE TO RELATED APPLICATION

This application is a 35 U.S.C. 371 National Phase Entry Application from PCT/JP2008/068421, filed Oct. 10, 2008, which claims the benefit of Japanese Patent Application No. 2007-265464 filed on Oct. 11, 2007, the disclosure of which is incorporated herein in its entirety by reference.

FIELD OF THE INVENTION

The present invention relates to a novel bis(trimethylsilyl)phenyl compound or a salt thereof, and application thereof.

BACKGROUND OF THE INVENTION

Physiological activities of retinoic acid are known to be induced by the adjustment of various gene expressions via a transcriptional control mechanism mediated by a nuclear receptor, i.e., retinoic acid receptor (hereinafter referred to as "RAR"). On the other hand, it is reported that high retinoid level conditions lead to a series of side effects, so-called retinoic acid syndrome, such as skin disorders, headaches, fatigue, and teratogenicity during pregnancy.

In malignant tumor patients, the amount of retinoic acid in the blood is reduced. Reduced physiological functions of retinoic acid are known to be associated with carcinogenesis, and the growth and progression of cancer. For this reason, extensive research has been conducted so far on compounds that have RAR agonistic activity and are hopefully useful for antitumor agents. For example, natural retinoic acid in nature: All-trans retinoic acid (hereinafter referred to as "ATRA") or metabolites thereof reportedly have physiological functions such as differentiation-inducing effects, and have a preventive effect on cancer; in addition, they are known as a treating agent for some diseases such as leukemia (Non-Patent Document 1). In recent years, among synthetic compounds other than ATRA, a compound group has been reported to have agonistic activity against RAR (collectively referred to as retinoids). Such compounds are expected to be used as pharmaceuticals.

RAR is known to be divided into three subtypes of $\alpha$, $\beta$, and $\gamma$, which have different expression states depending on cell species and tissues, controlling various vital functions. Among these types, RAR$\alpha$ is involved in cancer cell differentiation-inducing activity, cell-cycle arrest activity, apoptosis induction activity, etc. (Non-Patent Document 2); RAR$\beta$ is involved in teratogenicity (Non-Patent Document 3); and RAR$\gamma$ is involved in skin toxicity, bone toxicity, etc. (Non-Patent Document 4). Accordingly, a retinoid with high RAR$\alpha$ selectivity enhances antitumor effects and alleviates side effects induced by RAR$\gamma$, thereby boosting clinical profits.

4-[3,5-bis(trimethylsilyl)benzamido]benzoic acid (hereinafter referred to as "TAC-101") is a retinoid that has RAR$\alpha$ transcription-activating activity and cancer cell differentiation-inducing activity. Such a retinoid is known to be effective as antitumor agents, cancer cell differentiation-inducing agents, cancer metastasis inhibitors, therapeutic agents for diseases associated with angiogenesis, therapeutic agents for cardiac hypertrophy, etc. (e.g., Patent Documents 1 and 2). For example, TAC-101 has currently been under clinical development as orally-available antitumor agents. In a phase I study of non-small cell lung cancer, complete remission cases were reported, while symptoms (skin disorders) similar to hypervitaminosis A were observed (Non-Patent Document 5).

As stated above, it is desired to develop a retinoid that has high RAR$\alpha$ selectivity and is hardly bonded with RAR$\gamma$; in the clinical view, a pharmaceutical that has fewer side effects, such as skin disorders, and exerts a high antitumor effect.

Patent Document 1: Japanese Unexamined Patent Publication No. 1990-247185
Patent Document 2: International Publication No. WO 96/32101
Non-Patent Document 1: Journal of Clinical Oncology, 1992, May; 10(5), 839-864. Review.
Non-Patent Document 2: Blood. 1996 Mar. 1; 87(5), 1939-1950
Non-Patent Document 3: Development, 1991, November; 113(3), 723-734
Non-Patent Document 4: Am. J. Physiol., 1995, July; 269, E91-E98
Non-Patent Document 5: Journal of Clinical Oncology, Vol. 20, No. 16, 2002, 3522-3532

DESCRIPTION OF THE INVENTION

Problems to be Solved by the Invention

The present invention aims to provide a compound that exhibits an excellent antitumor effect and reduces side effects, such as skin disorders attributable to an existing retinoid, by selectively acting on the nuclear receptor RAR$\alpha$, thereby possibly producing significant improvement of clinical profits.

Means for Solving the Problems

The present inventors conducted extensive research to solve the above problems. As a result, they confirmed that a bis(trimethylsilyl)phenyl compound represented by Formula (I), described later, are excellent as compared to existing synthetic retinoid compounds. That is, (1) selective agonist activity against RAR$\alpha$ is superior;

(2) antitumor activity against cancer cells with high RAR$\alpha$ expression is apparently excellent;

(3) differentiation-inducing activity toward solid tumors and cancer malignancy (tumorigenicity) reducing activity are apparently excellent; and (4) skin toxicity is reduced due to attenuation of RAR$\gamma$ transcription-activating activity.

Specifically, the following facts were verified by constructing an RAR selective agonist activity measurement system using chimeric protein that fuses an agonist binding site of each RAR subtype and a DNA binding domain of a different transcription factor in pharmacological test examples, as described later. That is: a bis(trimethylsilyl)phenyl compound represented by Formula (I) or a salt thereof enhanced RAR$\alpha$ selective agonist activity more remarkably than ATRA or TAC-101 (Pharmacological Test Example 1); the compound had a remarkable tumor growth inhibitory effect in a hepatoma model with high RAR$\alpha$ expression, compared with TAC-101 (Pharmacological Test Example 2); and the compound induced differentiation of prostate cancer cells to neuroid cells and reduced cancer malignancy (Pharmacological Test Examples 3 and 4).

On the other hand, due to lower RAR$\gamma$ agonist activity, the bis(trimethylsilyl)phenyl compound represented by Formula (I) or a salt thereof can effectively reduce skin toxicity, which is one of typical retinoic acid syndromes, more so than TAC-101 (Pharmacological Test Example 5).

The present invention has been accomplished based on these findings.

The present invention provides a bis(trimethylsilyl)phenyl compound and use thereof according to the following Items 1 to 12:

Item 1. A bis(trimethylsilyl)phenyl compound represented by Formula (I):

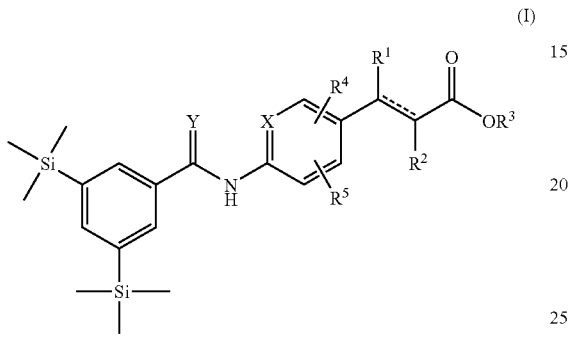

(I)

wherein X is N or CH;
Y is O or S;
$R^1$, $R^2$, and $R^3$ are the same or different and are hydrogen or lower alkyl;
$R^4$ and $R^5$ are the same or different and are hydrogen, lower alkyl, or halogen; and
a bond between a carbon atom to which $R^1$ is attached and a carbon atom to which $R^2$ is attached is a single bond or a double bond;
or a salt thereof.

Item 2. A bis(trimethylsilyl)phenyl compound according to Item 1 represented by Formula (IA):

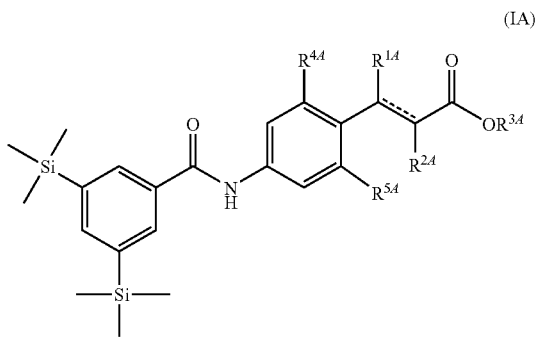

(IA)

wherein one of $R^{1A}$ and $R^{2A}$ is hydrogen and the other is lower alkyl, or both $R^{1A}$ and $R^{2A}$ are hydrogen;
$R^{3A}$ is hydrogen, methyl, or ethyl;
$R^{4A}$ is hydrogen, lower alkyl, or halogen;
$R^{5A}$ is hydrogen or halogen; and
a bond between a carbon atom to which $R^{1A}$ is attached and a carbon atom to which $R^{2A}$ is attached is a single bond or a double bond;
or a salt thereof.

Item 3. A bis(trimethylsilyl)phenyl compound according to Item 1 or 2 represented by Formula (IB):

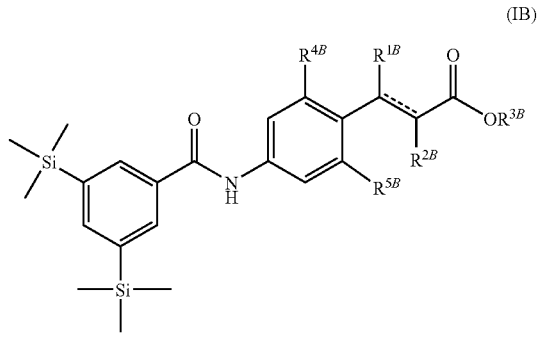

(IB)

wherein one of $R^{1B}$ and $R^{2B}$ is hydrogen and the other is methyl, or both $R^{1B}$ and $R^{2B}$ are hydrogen;
$R^{3B}$ is hydrogen or methyl;
$R^{4B}$ is hydrogen, methyl, fluorine, or chlorine;
$R^{5B}$ is hydrogen or fluorine; and
a bond between a carbon atom to which $R^{1B}$ is attached and a carbon atom to which $R^{2B}$ is attached is a single bond or a double bond;
or a salt thereof.

Item 4. A bis(trimethylsilyl)phenyl compound according to any one of Items 1 to 3 represented by Formula (IC):

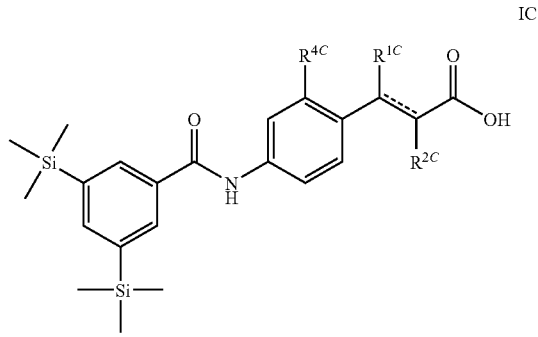

IC wherein one of $R^{1C}$ and $R^{2C}$ is hydrogen and the other is methyl, or both $R^{1C}$ and $R^{2C}$ are hydrogen;
$R^{4C}$ is hydrogen, methyl, fluorine, or chlorine; and
a bond between a carbon atom to which $R^{1C}$ is attached and a carbon atom to which $R^{2C}$ is attached is a double bond;
or a salt thereof.

Item 5. A bis(trimethylsilyl)phenyl compound according to any one of Items 1 to 4 represented by Formula (ID):

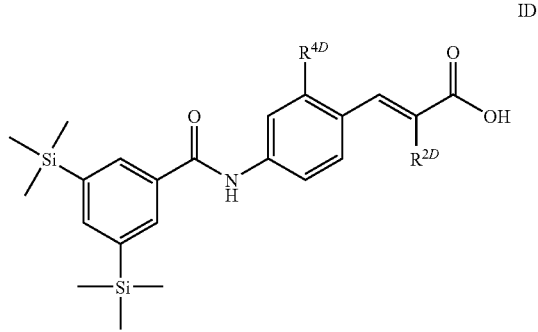

ID wherein $R^{2D}$ is methyl or hydrogen; and
$R^{4D}$ is hydrogen or fluorine;
or a salt thereof.

Item 6. A bis(trimethylsilyl)phenyl compound according to Item 1 or a salt thereof, wherein in Formula (I),
X is N or CH;
Y is S;
$R^1$ is lower alkyl or hydrogen;
$R^2$ is hydrogen;
$R^3$ is hydrogen, methyl, or ethyl;
both $R^4$ and $R^5$ are hydrogen; and
a bond between a carbon atom to which $R^1$ is attached and a carbon atom to which $R^2$ is attached is a single bond or a double bond.

Item 7. A bis(trimethylsilyl)phenyl compound according to Item 1 selected from the group consisting of:
4-[[3,5-bis(trimethylsilyl)benzoyl]amino]-2-fluorocinnamic acid;
4-[[3,5-bis(trimethylsilyl)benzoyl]amino]cinnamic acid;
3-[4-[[3,5-bis(trimethylsilyl)benzoyl]amino]phenyl]propanoic acid;
(E)-3-[4-[[3,5-bis(trimethylsilyl)benzoyl]amino]phenyl]-2-butenoic acid; and
(E)-3-[4-[[3,5-bis(trimethylsilyl)benzoyl]amino]-2-fluorophenyl]-2-methylacrylic acid;
or a salt thereof.

Item 8. A pharmaceutical composition comprising, as an active ingredient, a bis(trimethylsilyl)phenyl compound or a salt thereof according to any one of Items 1 to 7.

Item 9. An RARα agonist comprising, as an active ingredient, a bis(trimethylsilyl)phenyl compound or a salt thereof according to any one of Items 1 to 7.

Item 10. An antitumor agent comprising, as an active ingredient, a bis(trimethylsilyl)phenyl compound or a salt thereof according to any one of Items 1 to 7.

Item 11. A method for preventing or treating a disease that is effectively treated by an increase in RARα activity, the method comprising administering to a patient an effective amount of a bis(trimethylsilyl)phenyl compound or a salt thereof according to any one of Items 1 to 7.

Item 12. Use of a bis(trimethylsilyl)phenyl compound or a salt thereof according to any one of Items 1 to 7 for producing an agent for preventing or treating a disease that is effectively treated by an increase in RARα activity.

EFFECT OF THE INVENTION

The present invention provides a retinoid that has novel nuclear receptor RARα selective agonist activity. This retinoid exerts a superior antitumor effect and works on reducing side effects through RARα-selective transcription activation, and is therefore useful as an antitumor agent.
Specifically,
(1) the compound of the present invention shows a remarkably excellent antitumor effect as an orally-available antitumor agent as compared to existing retinoids; and
(2) the compound contributes to a significant reduction of skin toxicity that is one side effect of existing retinoids.
Diseases that can be treated by administering pharmaceutical preparations containing the compound of the present invention include malignant tumors, such as head and neck cancer, esophagus cancer, gastric cancer, colon cancer, rectal cancer, liver cancer, gallbladder and bile duct cancer, biliary tract cancer, pancreatic cancer, lung cancer, breast cancer, ovarian cancer, cervical cancer, endometrium cancer, renal cancer, bladder cancer, prostate cancer, testicular tumor, bone and soft-tissue sarcomata, leukemia, malignant lymphoma, multiple myeloma, skin cancer, brain tumor, mesothelioma, etc. Moreover, such pharmaceutical preparations containing the compound of the present invention are particularly effective in treating proliferative diseases caused by promoting differentiation and growth of cells, such as proliferative and immune malignant skin diseases accompanied by hyperkeratosis and inflammation, such as psoriasis, and immune diseases, such as rheumatism, and also effectively serve as an immunosuppressive agent for organ transplantation.

BEST MODE FOR CARRYING OUT THE INVENTION

Figure 1:
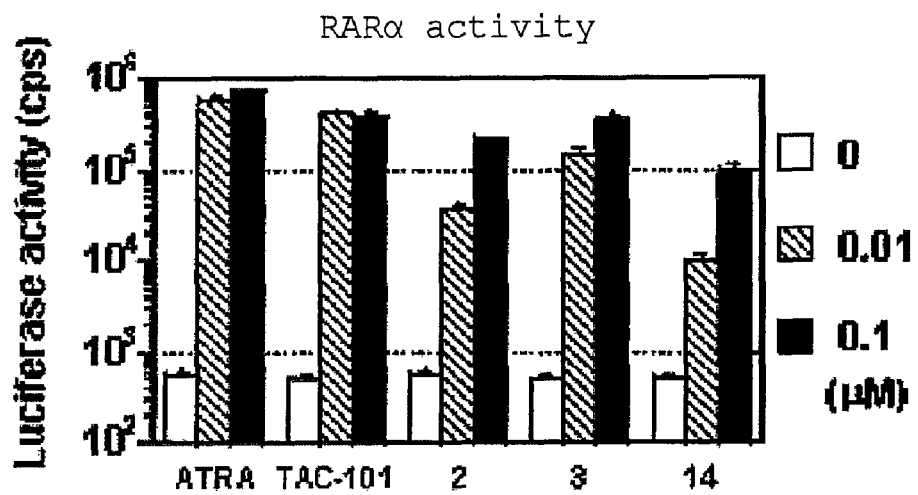
FIG. 1 is a graph showing the RARα selective transcription-activating activity.

The present invention is described in detail below.

Bis(trimethylsilyl)phenyl Compound

The bis(trimethylsilyl)phenyl compound of the present invention represented by the above-mentioned Formula (I) or a salt thereof is a novel compound having a structure in which a bis(trimethylsilyl)phenyl group and a phenylpropanoic acid compound or a phenylpropenoic acid compound are linked by an amide or thioamide bond.

For example, Patent Documents 1 and 2, and Non-Patent Document 5 disclose a bis(trimethylsilyl)phenyl compound having an RARα agonistic effect, which is useful as an antitumor agent. However, these documents merely teach a compound having a structure in which a bis(trimethylsilyl)phenyl group and a benzoic acid compound are linked by an amide bond, but does not mention the compound of the present invention, namely the structure in which a bis(trimethylsilyl)phenyl group and a phenylpropanoic acid compound or a phenylpropenoic acid compound are linked by an amide or thioamide bond. Moreover, it is not predictable from these documents that conversion of a benzoic acid compound into a phenylpropanoic acid compound or a phenylpropenoic acid compound improves RARα selectivity, enhances antitumor activity, and greatly reduces side effects, as shown in pharmacological test examples described below.

In Formula (I), X is CH or N, and is preferably CH.
In Formula (I), Y is oxygen or sulfur, and is preferably oxygen.
The "lower alkyl" represented by $R^1$ in Formula (I) is straight or branched $C_{1-6}$ alkyl, such as methyl, ethyl, n-propyl, isopropyl, n-butyl, sec-butyl, tert-butyl, n-pentyl, n-hexyl, etc, among which methyl is preferable. The "lower alkyl" represented by $R^{1A}$ in Formula (IA) is the same as above.
Examples of the "lower alkyl" represented by $R^2$ in Formula (I) include the above-mentioned lower alkyl, among which methyl is preferable. The "lower alkyl" represented by $R^{2A}$ in Formula (IA) is the same as above.

In the present invention, preferably, one of $R^1$ and $R^2$ is hydrogen and the other is lower alkyl, or both $R^1$ and $R^2$ are hydrogen. More preferably, both $R^1$ and $R^2$ are hydrogen.

Examples of the "lower alkyl" represented by $R^3$ in Formula (I) include the above-mentioned lower alkyl. Among them, methyl and ethyl are preferable, and methyl is more preferable.

Examples of the "lower alkyl" represented by $R^4$ and $R^5$ in Formula (I) include the above-mentioned lower alkyl, among which methyl is preferable. The "lower alkyl" represented by $R^{4A}$ in Formula (IA) is the same as above.

Examples of the "halogen" represented by $R^4$ and $R^5$ in Formula (I) include fluorine, bromine, chlorine, and iodine. Among them, fluorine and chlorine are preferable.

In the present invention, preferably, one of $R^4$ and $R^5$ is hydrogen and the other is halogen, or both are hydrogen. More preferably, both $R^4$ and $R^5$ are hydrogen.

When both $R^4$ and $R^5$ are halogen, the substitution position of $R^4$ and $R^5$ is preferably at the ortho and para positions relative to X. When one of $R^4$ and $R^5$ is halogen and the other is hydrogen, the substitution position of $R^4$ or $R^5$, whichever is halogen, is preferably at the ortho position relative to X.

The bond between the carbon atom to which $R^1$ is attached and the carbon atom to which $R^2$ is attached is a single bond or a double bond, and is preferably a double bond. When the bond between the carbon atom to which $R^1$ is attached and the carbon atom to which $R^2$ is attached is a double bond, the configuration is preferably the E configuration.

When the bond between the carbon atom to which $R^1$ is attached and the carbon atom to which $R^2$ is attached is a single bond, both $R^1$ and $R^2$ are preferably hydrogen.

When the bond between the carbon atom to which $R^1$ is attached and the carbon atom to which $R^2$ is attached is a double bond, preferably, one of $R^1$ and $R^2$ is hydrogen and the other is lower alkyl, or both $R^1$ and $R^2$ are hydrogen. More preferably, $R^1$ is hydrogen and $R^2$ is lower alkyl, and still more preferably, both $R^1$ and $R^2$ are hydrogen.

Particularly preferable compounds in the present invention are the following compounds or salts thereof:

4-[[3,5-bis(trimethylsilyl)benzoyl]amino]-2-fluorocinnamic acid;

4-[[3,5-bis(trimethylsilyl)benzoyl]amino]cinnamic acid;

3-[4-[[3,5-bis(trimethylsilyl)benzoyl]amino]phenyl]propanoic acid:

(E)-3-[4-[[3,5-bis(trimethylsilyl)benzoyl]amino]phenyl]-2-butenoic acid; and (E)-3-[4-[[3,5-bis(trimethylsilyl)benzoyl]amino]-2-fluorophenyl]-2-methylacrylic acid.

The bis(trimethylsilyl)phenyl compound represented by Formula (I) of the present invention includes stereoisomers, optical isomers, hydrates, and like solvates.

The bis(trimethylsilyl)phenyl compound represented by Formula (I) of the present invention may be a salt, and pharmacologically acceptable salts are preferable. Examples of such salts include salts of inorganic bases, salts of organic bases, salts with inorganic acids, salts with organic acids, salts with acidic amino acids, salts with basic amino acids, and the like.

Specifically, examples of salts of inorganic bases include sodium salts, potassium salts, and like alkali metal salts, and additionally, magnesium salts, calcium salts, and like alkaline earth metal salts.

Examples of salts of organic bases include trimethylamine, triethylamine, pyridine, N-methylpyridine, N-methylpyrrolidone, ethanolamine, diethanolamine, triethanolamine, dicyclohexylamine, etc.

Examples of inorganic acids include hydrochloric acid, sulfuric acid, hydrobromic acid, hydroiodic acid, nitric acid, phosphoric acid, etc.

Examples of organic acids include formic acid, acetic acid, propionic acid, malonic acid, succinic acid, glutaric acid, fumaric acid, maleic acid, lactic acid, malic acid, citric acid, tartaric acid, benzenesulfonic acid, p-toluenesulfonic acid, methanesulfonic acid, etc.

Examples of acidic amino acids include glutamic acid, aspartic acid, etc. Examples of basic amino acids include lysine, asparagine, ornithine, etc.

The bis(trimethylsilyl)phenyl compound represented by Formula (I) of the present invention may take the form of a pharmacologically acceptable prodrug. Any pharmacologically acceptable prodrugs are usable as long as they are convertible into the compound of Formula (I) under physiological conditions in the living body, e.g., by hydrolysis, oxidation, and reduction reactions by gastric acid or enzyme. Examples of such prodrugs include methyl ester, ethyl ester, propyl ester, phenyl ester, carboxy oxymethyl ester, and ethoxycarbonylester, and like ester type compounds that modify a carboxyl group. Typical examples that form these prodrugs include compounds convertible into Compound (I) under physiological conditions, as described in "Development of Pharmaceutical Products" (Hirokawa Shoten, 1990, Vol. 7 p. 163-198).

Moreover, the compound represented by Formula (I) of the present invention or a salt thereof includes various hydrates, various solvates, and crystal polymorphism thereof.

Bis(trimethylsilyl)phenyl Compound

Hereinafter, the compound represented by Formula (I) of the present invention can be produced by, for example, various methods as described below.

Process 1-1

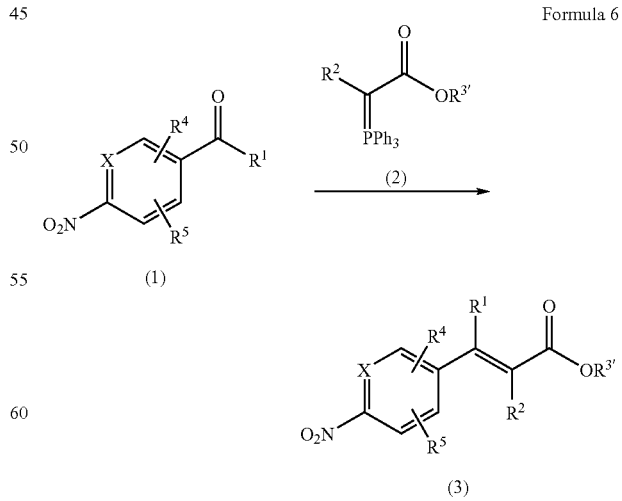

wherein X, $R^1$, $R^2$, $R^4$, and $R^5$ are the same as above, and $R^{3'}$ is lower alkyl.

A compound represented by Formula (3) can be produced from a compound represented by Formula (1) in accordance with methods disclosed in documents, e.g., B. E. Maryanoff et al., Chem. Rev. 1989, Vol. 89, p. 863-927, or methods based on the document. For example, the compound of Formula (3) can be obtained by reacting the compound of Formula (1) and an ylide compound represented by Formula (2) by means of the Wittig reaction. Examples of $R^{3'}$ include methyl, ethyl, n-propyl, and n-butyl, and like lower alkyl. Methyl and ethyl are preferable.

Both the compound of Formula (1) and the ylide compound of Formula (2), which are used as starting materials, may be known compounds or can be produced according to well-known methods.

The proportion of the compound of Formula (1) to the ylide compound of Formula (2) is generally 0.5 to 100 mol, and preferably 1 to 20 mol, based on 1 mol of the former compound.

This reaction is usually carried out in a suitable solvent. Reaction solvents are not limited as long as they do not affect the reaction. Examples of such solvents include benzene, n-hexane, carbon tetrachloride, acetone, methylene chloride, chloroform, methanol, toluene, tetrahydrofuran, diethyl ether, 1,4-dioxane, acetonitrile, 2-propanol, N,N-dimethylformamide, dimethyl sulfoxide, 1,2-dimethoxyethane, etc. They may be used as a single solvent or a mixed solvent.

The reaction temperature of the reaction is −100 to 150° C., and preferably 0 to 30° C. The reaction time is usually 0.1 to 100 hours.

Process 1-2

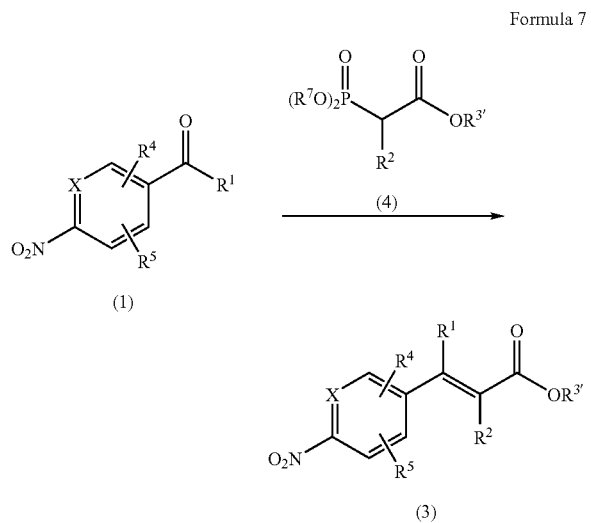

wherein X, $R^1$, $R^2$, $R^{3'}$, $R^4$, and $R^5$ are the same as above.

The compound represented by Formula (3) can also be produced by reacting the compound represented by Formula (1) and a phosphonate ester represented by Formula (4) by means of the Horner-Emmons reaction in the presence of base.

The phosphonate ester represented by Formula (4) may be a known one, or can be produced according to known methods.

Examples of $R^7$ include methyl, ethyl, n-propyl, phenyl, benzyl, etc. Methyl and ethyl are preferable.

The amount of the phosphonate ester of Formula (4) used is generally 0.5 to 100 equivalents, and preferably 1 to 20 equivalents, based on the compound of Formula (1).

Examples of bases include tert-butoxypotassium, sodium hydride, potassium hydride, n-butyl lithium, potassium carbonate, lithium hydroxide, lithium chloride, diisopropylethylamine, potassium hexamethyldisilazide, sodium hexamethyldisilazide, lithium diisopropylamine, 1,8-diazabicyclo[5.4.0]-7-undecene, potassium carbonate, and the like. The amount of the base used is generally 0.5 to 100 equivalents, and preferably 1 to 20 equivalents, based on the compound of Formula (1).

A reaction accelerator may be present in the reaction system in the present invention. Examples of reaction accelerators include 18-crown-6,15-crown-5, tetra-n-hexylammonium bromide, potassium fluoride, magnesium oxide, zinc oxide, etc. The amount of the reaction accelerator used is usually 0.5 to 100 equivalents, and preferably 1 to 20 equivalents, based on the compound of Formula (1).

Reaction solvents are not limited as long as they do not affect the reaction. Examples of such solvents include benzene, n-hexane, carbon tetrachloride, acetone, methylene chloride, chloroform, methanol, toluene, tetrahydrofuran, diethyl ether, 1,4-dioxane, acetonitrile, 2-propanol, N,N-dimethylformamide, dimethyl sulfoxide, 1, 2-dimethoxyethane, etc. They may be used as a single solvent or a mixed solvent.

The reaction temperature of the reaction is usually −100 to 150° C., and preferably 0 to 30° C. The reaction time is usually 0.1 to 100 hours.

Although the compound of Formula (3) obtained by this reaction may optionally be isolated and purified by known separation and purification procedures, it may be used in the next process without purification.

Process 2

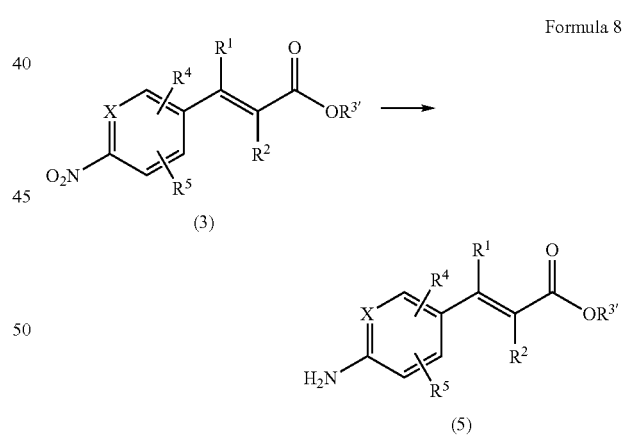

wherein X, $R^1$, $R^2$, $R^{3'}$, $R^4$, and $R^5$ are the same as above.

The compound represented by Formula (3) can be converted into an amine represented by Formula (5) by means of the catalytic reduction method using metal catalysts, the reduction method by metals or salts thereof, and the reduction method by hydride compounds and hydrazine compounds.

When the catalytic reduction method using metal catalysts is carried out, for example, Raney nickel, palladium-carbon, platinum oxide, etc., are usable as a catalyst. In this case, hydrogen is mainly used as a reducing agent, which can be substituted by ammonium formate or like formates, hydrazine, sodium borohydride, cyclohexene, etc. When using hydrogen, the pressure is 1 to 100 atm. In this case, solvents are not limited as long as they do not affect the reaction. Examples thereof include ethanol, methanol and like alcohols, ethyl acetate, and like esters, and N,N-dimethylformamide, chloroform, dichloromethane, diethyl ether, acetic acids, etc. They may be used singly or in combination.

When the reduction method by metals or salts thereof is employed, iron, zinc, tin, samarium, indium, etc., are usable as metal. The amount of the metal used is usually 0.5 to 100 equivalents, and preferably 1 to 20 equivalents, based on the compound of Formula (3).

This reaction is usually carried out in a suitable solvent. Solvents are not limited as long as they do not affect the reaction. Examples thereof include acetic acid, hydrochloric acid solution, tetrahydrofuran, methanol, ethanol, etc. They may be used singly or in combination.

When the reduction by hydride compounds is carried out, lithium aluminum hydride, hydrogenation boron lithium, etc., are usable as a hydride compound. The amount of the hyydride compound used is usually 0.5 to 100 equivalents, and preferably 1 to 20 equivalents, based on the compound of Formula (3).

This reaction is usually carried out in a suitable solvent. Solvents are not limited as long as they do not affect the reaction. Examples thereof include tetrahydrofuran, methanol, ethanol, etc. They may be used singly or in combination.

When the reduction by hydrazine compounds is performed, hydrazine, phenylhydrazine, etc., are usable as a hydrazine compound. The amount of the hydrazine compound used is usually 0.5 to 100 equivalents, and preferably 1 to 20 equivalents, based on the compound of Formula (3).

This reaction is usually carried out in a suitable solvent. Solvents are not limited as long as they do not affect the reaction. Examples thereof include methanol, ethanol, and like alcohols, etc.

Moreover, the amine represented by Formula (5) can also be synthesized by a method as described in Process 3 below. Although the compound of Formula (5) obtained by this reaction may optionally be isolated and purified by known separation and purification procedures, it may be used in the next process without purification.

Process 3

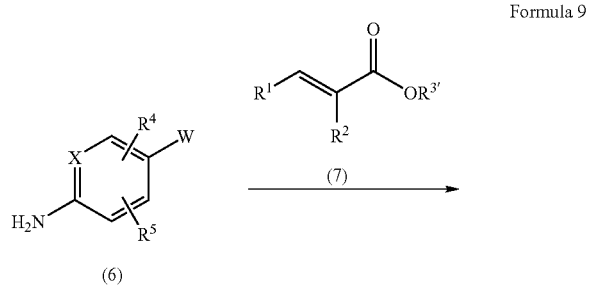

Formula 9 wherein X, $R^1$, $R^2$, $R^{3'}$, $R^4$, and $R^5$ are the same as above, and W is halogen.

The compound represented by Formula (5) can be produced by reacting an easily available compound (6) and an acrylic acid compound represented by Formula (7) in the presence of a zerovalent palladium precursor, a phosphine ligand, and a base, in accordance with methods disclosed in documents, e.g., Heck, R. F. Org. React. 1982, Vol. 27, p. 345-390 (Review), or methods based on the document.

The acrylic acid compound represented by Formula (7) may be a known one, or can be produced according to a known method.

Examples of $R^{3'}$ include methyl, ethyl, n-propyl, n-butyl, etc. Methyl and ethyl are preferable.

Palladium acetate is generally used as a zerovalent palladium precursor. The amount of the zerovalent palladium precursor used is usually 0.001 to 20 equivalents, and preferably 0.01 to 10 equivalents, based on the compound of Formula (6).

Examples of phosphine ligands include triphenylphosphine, tris(2-methylphenyl)phosphine, tri-n-butyl phosphine, etc. The amount of the phosphine ligand used is generally 0.01 to 20 equivalents, and preferably 0.05 to 10 equivalents, based on the compound of Formula (6).

The proportion of Compound (6) to the acrylic acid compound of Formula (7) is generally 0.5 to 100 mol, and preferably 1 to 50 mol, based on the 1 mol of the former compound.

Reaction solvents are not limited as long as they do not affect the reaction. Examples thereof include acetonitrile, toluene, pyridine, tetrahydrofuran, 1,4-dioxane, diethyl ether, N,N-dimethylformamide, N,N-dimethylacetamide, dimethyl sulfoxide, etc. They are used as a single solvent or a mixed solvent.

Moreover, examples of bases for use in the condensation reaction include trimethylamine, triethylamine, pyridine, picoline, collidine, lutidine, N-methylmorpholine, N-methylpyrrolidine, diisopropylethylamine, etc. The amount of the base used is usually 0.1 to 200 equivalents, and preferably 0.5 to 100 equivalents, based on the compound of Formula (6).

This reaction is usually carried out at a temperature ranging from 0° C. to about the boiling point of the solvent used.

The reaction time is usually 0.5 to 100 hours, and preferably 1 to 20 hours.

The compound of Formula (5) obtained by this reaction may optionally be isolated and purified by known separation and purification procedures.

The compounds of the present invention, namely the compounds represented by Formulae (1a) to (1h), can be obtained by any one of Processes 4 to 11 as described below.

Process 4

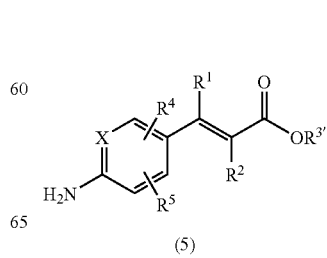

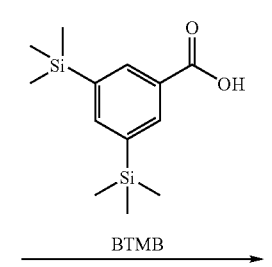

Formula 10

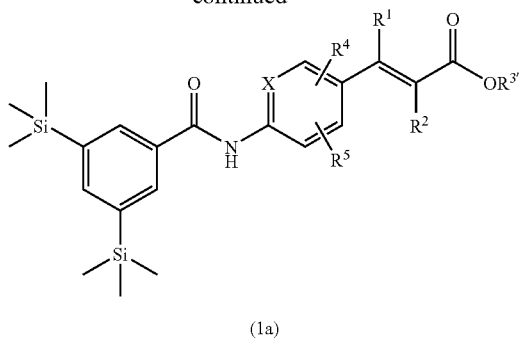

(1a)

wherein X, $R^1$, $R^2$, $R^{3'}$, $R^4$, and $R^5$ are the same as above.

Among the compounds of the present invention, the compound represented by Formula (1a), wherein corresponding $R^3$ is lower alkyl, Y is O, and the bond between the carbon atom to which $R^1$ is attached and the carbon atom to which $R^2$ is attached is a double bond, can be produced by condensing the compound represented by Formula (5) and the known compound 3,5-bis trimethylsilyl benzoic acid (hereinafter referred to as "BTMB"). BTMB can be produced in accordance with methods disclosed in documents, e.g., Takeru Yamakawa. et al. J. Med. Chem., 1990, vol. 33, No. 5.

The condensation reaction can be performed in accordance with usual acid-base condensation reaction, an acid chloride method, a mixed acid anhydride method, or a method using a dehydration condensation agent, etc.

The proportion of BTMB to the compound of Formula (5) is usually 0.1 to 100 mol, and preferably 1 to 20 mol, based on 1 mol of BTMB.

Examples of condensing agents usable in the condensation reaction include 1-(3-dimethylaminopropyl)-3-ethylcarbodiimide hydrochloride, dicyclohexylcarbodiimide, 4-(4,6-dimethoxy-1,3,5-triazine-2-yl)-4-methylmorpholinium chloride, and the like. The amount of the condensing agent used is usually 0.5 to 100 equivalents, and preferably 1 to 20 equivalents, based on the compound of Formula (5).

Examples of reaction agents usable in the mixed acid anhydride method include ethyl chlorocarbonate, isobutyl chlorocarbonate, trichloroethyl chloroformate, acetic anhydride, triphosgene, oxalyl dichloride, thionyl chloride, phosphorus trichloride, phosphorus pentachloride, phosphorus oxychloride, and the like. The amount of the reaction agent used is usually 0.01 to 100 equivalents, and preferably 0.1 to 20 equivalents, based on the compound of Formula (5).

Bases usable in the condensation reaction are not limited as long as they do not affect an ester. As organic bases, for example, trimethylamine, triethylamine pyridine, picoline, collidine, lutidine, N-methyl morpholine, N-methylpyrrolidine, diisopropylethylamine, etc., are usable. As inorganic bases, for example, potassium carbonate, sodium carbonate, etc., are usable. The amount of the base used is usually 0.05 to 100 equivalents, and preferably 0.1 to 20 equivalents, based on the compound of Formula (5).

The reaction can usually be carried out in a suitable solvent as long as the solvent does not affect the reaction. Examples of such solvent include acetonitrile, toluene, pyridine, methanol, ethanol, dichloromethane, chloroform, ethyl acetate, tetrahydrofuran, dioxane, diethyl ether, N,N-dimethylformamide, N,N-dimethylacetamide, dimethyl sulfoxide, etc.

Moreover, the reaction is performed at a reaction temperature ranging from −20° C. to below reflux temperature of the solvent used.

The reaction time is usually 0.5 to 100 hours, and preferably 1 to 20 hours.

Although the compound of Formula (1a) obtained by this reaction may optionally be isolated and purified by known separation and purification procedures, it may be used in the next process without purification.

Process 5

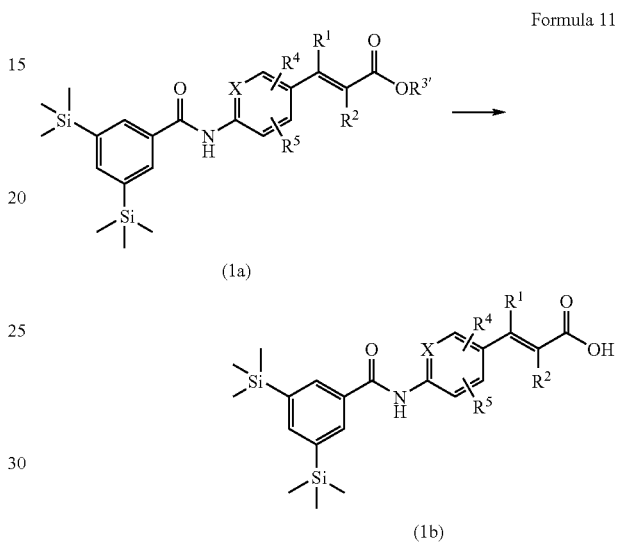

wherein X, $R^1$, $R^2$, $R^{3'}$, $R^4$, and $R^5$ are the same as above.

Among the compounds of the present invention, the compound represented by Formula (1b), wherein corresponding $R^3$ is hydrogen, Y is O, and the bond between the carbon atom to which $R^1$ is attached and the carbon atom to which $R^2$ is attached is a double bond, can be produced from the compound represented by Formula (1a) by means of generally-used elimination reaction of protective group(s) of carboxyl group.

For example, acid or alkali hydrolysis, reductive deprotection reaction, desorption by Lewis acid, etc., are applicable.

Acids usable in hydrolysis reaction are not limited as long as they do not affect the reaction. Examples of such acids include hydrochloric acid, sulfuric acid, hydrobromic acid, formic acid, acetic acid, etc. Examples of bases include sodium hydrate, potassium hydroxide, lithium hydroxide, and like alkali metal salts, sodium methylate, sodium ethylate, and like alkoxy metal salts, etc. The preferable hydrolysis for the reaction is basic hydrolysis.

The preferable amount of the acid or base used is usually about 0.1 to 5 equivalents based on the compound of Formula (1a).

Solvents usable in the reaction are not limited as long as they do not affect the reaction. Example thereof include water, methanol, ethanol, 1-propanol, 2-propanol, acetonitrile, toluene, pyridine, tetrahydrofuran, 1,4-dioxane, diethyl ether, N,N-dimethylformamide, N,N-dimethylacetamide, dimethyl sulfoxide, etc. They may be used as a single solvent or a mixed solvent. A single solvent or mixed solvent of water, methanol, and ethanol are preferable in the reaction.

Moreover, the reaction is performed at a reaction temperature ranging from −20° C. to reflux temperature of the solvent used. The reaction time is usually 0.5 to 100 hours, and preferably 1 to 20 hours. Although the compound of Formula (1b) obtained by this reaction may optionally be isolated and purified by known separation and purification procedures, it may be used in the next process without purification.

Process 6

Although the compound of Formula (1c) obtained by this reaction may optionally be isolated and purified by known separation and purification procedures, it may be used in the next process without purification.

Process 7

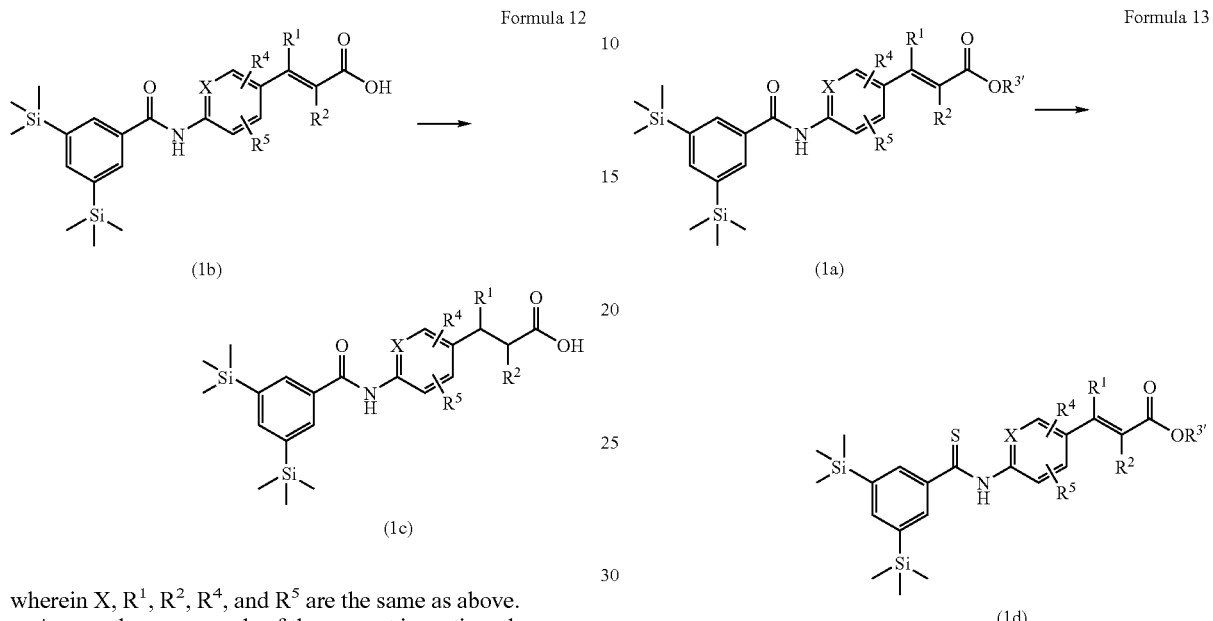

wherein X, $R^1$, $R^2$, $R^4$, and $R^5$ are the same as above.

Among the compounds of the present invention, the compound represented by Formula (1c), wherein corresponding $R^3$ is hydrogen, Y is O, and the bond between the carbon atom to which $R^1$ is attached and the carbon atom to which $R^2$ is attached is a single bond, can be produced from the compound represented by Formula (1b) by means of a generally-used method as a reduction reaction of the double bond. For example, heterogeneous reduction reaction employs a method in which hydrogenation is conducted in a suitable solvent in the presence of a palladium-carbon catalyst.

As usable metal, palladium, palladium hydroxide, platinum oxide, cadmium, copper, etc., are exemplified. Moreover, homogeneous reduction reaction employs a rhodium catalyst or ruthenium catalyst as typified by the Wilkinson catalyst.

Solvents usable in reaction are not limited as long as they do not affect the reaction. Examples thereof include water, methanol, ethanol, 1-propanol, 2-propanol, ethyl acetate, tetrahydrofuran, 1,4-dioxane, diethyl ether, acetic acid, toluene, benzene, N,N-dimethylformamide, N,N-dimethylacetamide, etc. They may be used singly or in combination. A single solvent or mixed solvent of water, methanol, and ethanol are preferable in the reaction.

The reaction is performed at a reaction temperature ranging from −20° C. to reflux temperature of the solvent used. The reaction time is usually 0.5 to 100 hours, and preferably 1 to 20 hours.

Moreover, in the reduction reaction of hydrogenation, the reaction can also be carried out under ordinary pressure or increased pressure. Additionally, the reaction can employ formic acid, ammonium formate, cyclohexene, hydrazine, and like inorganic salts as a hydride source in the presence of the above-mentioned metal catalysts. The amount of the inorganic salt used is usually 0.5 to 100 equivalents, and preferably 1 to 20 equivalents, based on the compound of Formula (1b).

wherein X, $R^1$, $R^2$, $R^{3'}$, $R^4$, and $R^5$ are the same as above.

Among the compounds of the present invention, the compound represented by Formula (1d), wherein corresponding $R^3$ is lower alkyl, Y is S, and the bond between the carbon atom to which $R^1$ is attached and the carbon atom to which $R^2$ is attached is a double bond, can be led from the compound of Formula (1a) using hydrogen sulfide, phosphorus pentasulfide, boron sulfide, phosphoryl bromide, Lawesson's reagents, and the like.

The compound represented by Formula (1d) can be produced in accordance with methods using a Lawesson's reagent as disclosed in documents, e.g., M. Jesberger. Synthesis, 2003, Vol. 12, p. 1920-1927 (Review), or methods based on the document.

Reaction solvents are not limited as long as they do not affect the reaction. Examples thereof include toluene, xylene, pyridine, tetrahydrofuran, 1,2-dimethoxyethane, benzene, acetonitrile, 1,4-dioxane, hexamethylphosphoric triamide, etc. They may be used as a single solvent or a mixed solvent.

Moreover, the reaction is performed at a reaction temperature ranging from 0° C. to reflux temperature of the solvent used.

The reaction time is usually 0.5 to 100 hours, and preferably 1 to 20 hours. Although the compound of Formula (1d) obtained by this reaction may optionally be isolated and purified by known separation and purification procedures, it may be used in the next process without purification.

Process 8

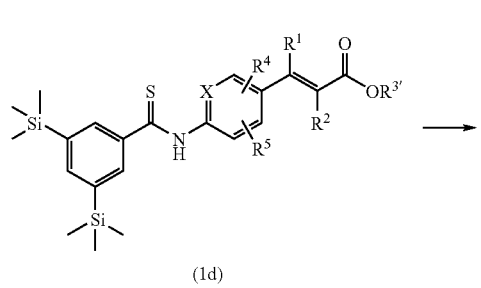

wherein X, $R^1$, $R^2$, $R^{3'}$, $R^4$, and $R^5$ are the same as above.

A reaction of Process 8 is carried out under the same reaction conditions as the reaction of Process 5.

Process 9

Formula 15

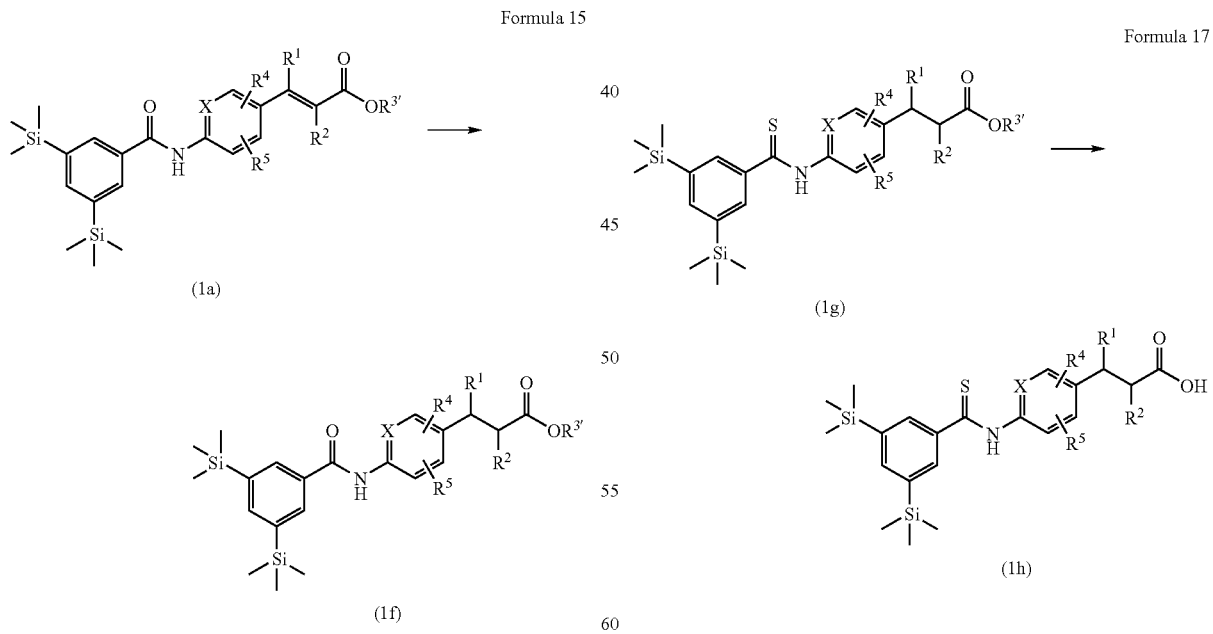

wherein X, $R^1$, $R^2$, $R^{3'}$, $R^4$, and $R^5$ are the same as above.

A reaction of Process 9 is carried out under the same reaction conditions as the reaction of Process 6.

Process 10

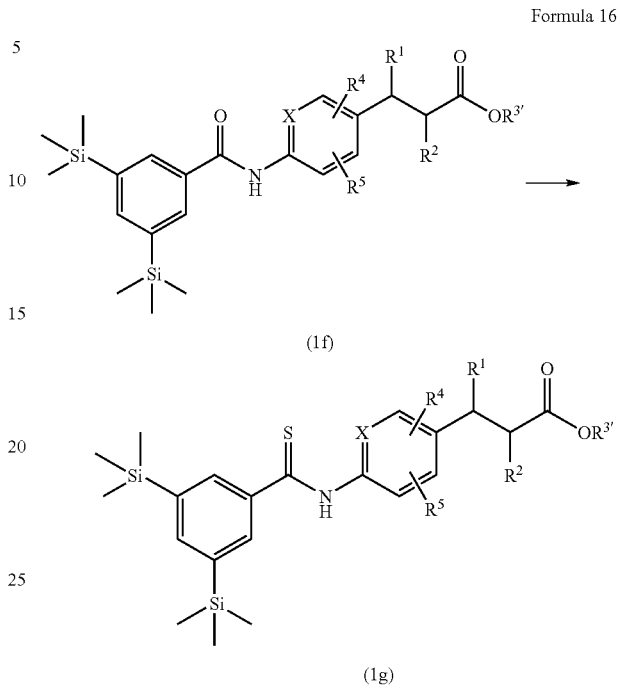

wherein X, $R^1$, $R^2$, $R^{3'}$, $R^4$, and $R^5$ are the same as above.

A reaction of Process 10 is carried out under the same reaction conditions as the reaction of Process 7.

Process 11

Formula 17 wherein X, $R^1$, $R^2$, $R^{3'}$, $R^4$, and $R^5$ are the same as above.

A reaction of Process 11 is carried out under the same reaction conditions as the reaction of Process 5.

As described above, the compounds of the present invention and the synthetic intermediates thus obtained can generally be purified and isolated by known separation and purification means, such as recrystallization, crystallization, distillation, column chromatography, and the like. The compounds of the present invention and the synthetic intermediates can generally form pharmacologically acceptable salts thereof according to known methods, and they are mutually convertible.

When used as a medicine, Compound (I) of the present invention may optionally be mixed with a pharmacological carrier. Depending on the purpose of prevention or treatment, various dosage forms are adoptable. The dosage form may be, for example, an oral formulation, injection, suppository, ointment, patch, etc. An oral agent is preferable. Such dosage forms can be produced according to common preparation methods known to those skilled in the art.

As the pharmacological carrier, various organic or inorganic carrier materials commonly used as pharmaceutical raw materials, are usable. These are mixed as excipients, binders, disintegrators, lubricants, or colorants in solid formulations, or as solvents, solubilizing agents, suspending agents, isotonizing agents, buffers, or soothing agents in liquid formulations. If necessary, other pharmaceutical additives such as preservatives, antioxidants, colorants, sweeteners, stabilizing agents, and the like may also be used.

Oral solid formulations are prepared as follows. An excipient, optionally together with an excipient binder, disintegrant, lubricant, colorant, sweetening/flavoring agent, etc., are added into the compound of the present invention to produce tablets, coated tablets, granules, powders, capsules, or the like using a standard method.

Examples of usable excipients include lactose, sucrose, D-mannitol, glucose, starch, calcium carbonate, kaolin, microcrystalline cellulose, silicic acid anhydride, etc.

Examples of usable binders include water, ethanol, 1-propanol, 2-propanol, simple syrup, liquid glucose, liquid α-starch, liquid gelatin, D-mannitol, carboxymethyl cellulose, hydroxypropyl cellulose, hydroxypropyl starch, methyl cellulose, ethyl cellulose, shellac, calcium phosphate, polyvinylpyrrolidone, etc.

Examples of usable disintegrants include dry starch, sodium alginate, agar powder, sodium hydrogen carbonate, calcium carbonate, sodium lauryl sulfate, stearic acid monoglyceride, lactose, etc.

Examples of usable lubricants include purified talc, stearate sodium, magnesium stearate, borax, polyethylene glycol, etc.

Examples of usable colorants include titanium oxide, iron oxide, etc.

Examples of usable sweetening/flavoring agents include sucrose, wild orange peel, citric acid, tartaric acid, etc.

Liquid oral formulations are produced as follows. A sweetening agent, buffer, stabilizer, flavoring agent, etc., are added into the compound of the present invention to produce internal liquid medicines, syrups, elixirs, or the like using a standard method. In this case, sweetening/flavoring agents as described above are usable. Examples of usable buffers include sodium citrate etc., and examples of usable stabilizers include tragacanth, gum arabic, gelatin, etc. If necessary, enteric coating or other coating by a known method may be applied on the oral formulation for a longer-lasting effect. Examples of such coating agents include hydroxypropylmethylcellulose, ethyl cellulose, hydroxymethylcellulose, hydroxypropylcellulose, polyoxyethylene glycol, Tween 80™, etc.

Injections are prepared as follows. A pH adjustor, buffer, stabilizer, isotonizing agent, topical anesthetic, etc., are added into the compound of the present invention to produce subcutaneous injections, intramuscular injections, or intravenous injections using a standard method. Examples of usable pH adjusters and buffers in this case include sodium citrate, sodium acetate, sodium phosphate, etc. Examples of usable stabilizers include sodium pyrosulfite, EDTA, thioglycolic acid, thiolactic acid, etc. Examples of usable topical anesthetics include procaine hydrochloride, lidocaine hydrochloride, etc. Examples of usable isotonizing agents include sodium chloride, glucose, D-mannitol, glycerin, etc.

Suppositories are prepared as follows. Pharmaceutical carriers known in the art, such as polyethylene glycol, lanolin, cacao butter, fatty acid triglyceride, etc., are added into the compound of the present invention, optionally together with Tween 80™ and like surfactants, etc., followed by production using a standard method.

Ointments are prepared as follows. An ordinary base, stabilizer, wetting agent, preservative, etc., are added as required into the compound of the present invention, and mixed and formulated using a standard method. Examples of usable bases include liquid paraffin, white vaseline, white beeswax, octyldodecyl alcohol, paraffin, etc. Examples of usable preservatives include methyl parahydroxybenzoate, ethyl parahydroxybenzoate, propyl parahydroxybenzoate, etc.

Patches can be prepared by coating an ordinary support with the above ointment, cream, gel, paste, etc., using a standard method. Examples of usable supports include woven or nonwoven fabrics made from cotton, staple fibers, and chemical fibers; and films or foam sheets of soft vinyl chloride, polyethylene, polyurethane, etc.

The amount of the compound of the present invention to be contained in such a dosage unit form varies depending on the condition of the subject patient or on the dosage form. The desirable amount in one dosage unit form is about 0.05 to 1000 mg in the case of an oral formulation, about 0.01 to 500 mg in the case of an injection, and about 1 to 1000 mg in the case of a suppository.

The daily dose of the medicine in such a dosage form depends on the condition, body weight, age, gender, and the like of the patient. For example, the daily dose for an adult (body weight: 50 kg) is usually about 0.05 to 5000 mg, and preferably 0.1 to 1000 mg, and is preferably administered at once or in two or three divided doses per day.

EXAMPLES

The present invention is described below in more detail with reference to examples, pharmacological test examples, and formulation examples. However, the present invention is not limited to these examples.

Example 1

Ethyl 3-(6-aminopyridine-3-yl)acrylate (1a)

2-Amino-5-bromopyridine (15 g) was dissolved in a mixed solvent of N,N-dimethylformamide (hereinafter referred to as "DMF"; 60 ml) and N,N-diisopropylethylamine (60 ml). Ethyl acrylate (12 ml), palladium acetate (980 mg), and tris(2-methylphenyl)phosphine (10.5 g) were added thereto in a nitrogen atmosphere, and the mixture was stirred at 100° C. for 12 hours. The reaction mixture was filtered through Celite and separated with ethyl acetate and water. The organic layer was washed with a saturated sodium chloride solution, and then dried over anhydrous sodium sulfate. The solvent was distilled off, and the residue was crystallized with N-hexane to obtain Compound 1a (15.5 g, 89%) as a yellow solid.

$^1$H-NMR (CDCl$_3$) δ8.20 (1H, s), 7.66 (1H, dd, J=2.3 Hz, J=8.5 Hz), 7.57 (1H, d, J=16.1 Hz), 6.51 (1H, d, J=8.5 Hz), 6.25 (1H, d, J=16.1 Hz), 4.72 (2H, brs), 4.24 (2H, q, J=7.1

Hz), 1.33 (3H, t, J=7.1 Hz), 1.33 (3H, t, J=7.1 Hz); FAB-LRMS (negative) m/z 191 (M-H)⁻.

(E)-Ethyl 3-[6-[[3,5-bis(trimethylsilyl)benzoyl]amino]-pyridin-3-yl]acrylate (1b)

3,5-Bis(trimethylsilyl)benzoic acid (hereinafter referred to as "BTMB"; 700 mg) was suspended in acetonitrile (5.25 ml) in a nitrogen atmosphere. Pyridine (0.212 ml) and Compound 1a (603 mg) were added to the suspension, and phosphorus oxychloride (0.131 ml) was added dropwise under ice-cooling. The mixture was stirred while refluxing under heating for 3.5 hours. After the reaction mixture was allowed to cool, water and ethyl acetate were added thereto. The organic layer was washed three times with water and once with a saturated sodium chloride solution, and then dried over anhydrous sodium sulfate. The solvent was distilled off, and the residue was purified by neutral silica gel column chromatography (5% ethyl acetate/n-hexane) to obtain Compound 1b (232 mg, 20%) as a white foam.

$^1$H-NMR (CDCl$_3$) δ8.70 (1H, s), 8.47 (1H, d, J=8.6 Hz), 8.43 (1H, s), 8.00 (2H, s), 7.96 (1H, d, J=8.6 Hz), 7.85 (1H, s), 7.66 (1H, d, J=15.9 Hz), 6.46 (1H, d, J=15.9 Hz), 4.28 (2H, q, J=7.0 Hz), 1.35 (3H, t, J=7.0 Hz), 0.33 (18H, s); FAB-LRMS m/z 441 (MH⁺).

(E)-3-[6-[[3,5-Bis(trimethylsilyl)benzoyl]amino]-pyridin-3-yl]acrylic acid (1)

Compound 1b (232 mg) was dissolved in ethanol (7.89 ml). A 2N sodium hydroxide aqueous solution (5.26 ml) was added thereto and the mixture was stirred at room temperature overnight. The reaction mixture was ice-cooled, and a 2N hydrochloric acid aqueous solution (5.26 ml) was added to neutralize the mixture. Then the solvent was distilled off. The reaction mixture was ice-cooled, and a 2N hydrochloric acid aqueous solution (0.5 ml) was added to adjust the pH of the mixture to 1. The mixture was stirred for 1 hour. The precipitated solid was filtered off and vacuum-dried to give Compound 1 (88.0 mg, 41%) as a white solid.

$^1$H-NMR (DMSO-d$_6$) δ11.19 (1H, s), 8.68 (1H, s), 8.29-8.23 (2H, m), 8.14 (2H, s), 7.82 (1H, s), 7.61 (1H, d, J=16.2 Hz), 6.61 (1H, d, J=16.2 Hz), 0.32 (18H, s); FAB-LRMS m/z 413 (MH⁺); mp 302° C. (decomp.).

Formula 18

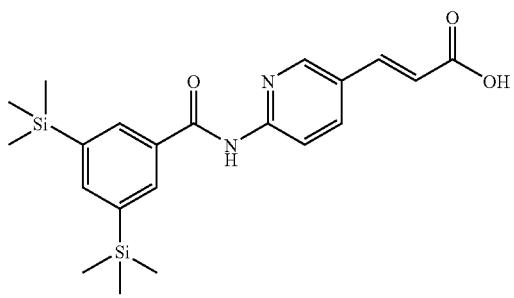

Example 2

Ethyl 4-amino-2-fluorocinnamate (2a)

4-Bromo-3-fluoroaniline (5.0 g) was dissolved in a mixed solvent of DMF (18 ml) and N,N-diisopropylethylamine (18 ml). Ethyl acrylate (3.9 ml), palladium acetate (295 mg), and tris(2-methylphenyl) phosphine (3.2 g) were added to the obtained mixture in a nitrogen atmosphere, and the mixture was stirred at 110° C. for 5 hours. The reaction mixture was filtered through Celite and separated with ethyl acetate and water. The organic layer was washed with a saturated sodium chloride solution, and then dried over anhydrous sodium sulfate. The solvent was distilled off, and the residue was purified by neutral silica gel column chromatography (14-25% ethyl acetate/n-hexane). The purified material was crystallized with n-hexane to obtain Compound 2a (4.2 g, 76%) as a yellow solid.

$^1$H-NMR (DMSO-d$_6$) δ7.54 (1H, d, J=15.9 Hz), 7.46 (1H, t, J=8.6 Hz), 6.39 (1H, dd, J=2.2 Hz, J=8.5 Hz), 6.32 (1H, dd, J=2.2 Hz, J=13.9 Hz), 6.24 (1H, d, J=15.9 Hz), 6.10 (2H, brs), 4.14 (2H, q, J=7.1 Hz), 1.22 (3H, t, J=7.1 Hz); FAB-LRMS (negative) m/z 208 (M-H)⁻.

Ethyl 4-[[3,5-bis(trimethylsilyl)benzoyl]amino]-2-fluorocinnamate (2b)

BTMB (266 mg) was suspended in acetonitrile (2 ml), and pyridine (80 μl) and Compound 2a (251 mg) were added thereto. Phosphorus oxychloride (50 μl) was added dropwise at 0° C. in a nitrogen atmosphere, and the mixture was stirred under reflux conditions for 4 hours. The reaction mixture was crystallized with water (2.7 ml). The obtained solid was suspended in isopropyl alcohol (270 μl) and pulverized with ultrasonic waves. The solid was filtered off and washed twice with isopropyl alcohol (270 μl). Thus, Compound 2b (265 mg, 57%) was obtained as a light yellow solid.

$^1$H-NMR (CDCl$_3$) δ7.90 (2H, s), 7.83 (2H, m), 7.78-7.71 (2H, m), 7.52 (1H, t, J=8.3 Hz), 7.30 (1H, dd, J=2.0 Hz, J=8.3 Hz), 6.48 (1H, d, J=16.1 Hz), 4.26 (2H, q, J=7.1 Hz), 1.33 (3H, t, J=7.1 Hz), 0.31 (18H, s); FAB-LRMS m/z 458 (MH⁺).

4-[[3,5-Bis(trimethylsilyl)benzoyl]amino]-2-fluorocinnamic acid (2)

Compound 2b (80 mg) was dissolved in ethanol (2.6 ml), and a 2N sodium hydroxide aqueous solution (1.7 ml) was added to the obtained solution in a nitrogen atmosphere. The mixture was stirred overnight at room temperature. A 2N hydrochloric acid aqueous solution (3.4 ml) was added thereto. The resulting white precipitate was filtered off and dissolved in ethyl acetate. The reaction mixture was separated with ethyl acetate and water. The organic layer was washed with a saturated sodium chloride solution, and then dried over anhydrous sodium sulfate. After the solvent was distilled off and n-hexane was added to the obtained residue, the mixture was pulverized with ultrasonic waves. The solid was filtered off, and the obtained powder was dissolved in butyl acetate (0.5 ml) by heating. The reaction mixture was allowed to cool and then filtered. Thus, Compound 2 (39 mg, 55%) was obtained as an opalescent solid.

$^1$H-NMR (DMSO-d$_6$) δ12.44 (1H, brs), 10.59 (1H, s), 8.01 (2H, s), 7.84 (3H, m), 7.59 (2H, m), 6.53 (1H, d, J=16.1 Hz), 0.31 (18H, s); FAB-LRMS m/z 430 (MH⁺).

Formula 19

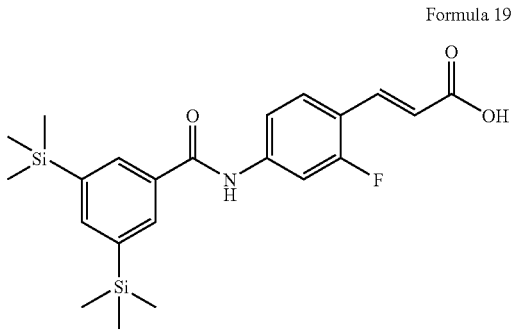

Example 3

Ethyl 4-[[3,5-bis(trimethylsilyl)benzoyl]amino]cinnamate (3a)

Using BTMB (10.0 g) and ethyl 4-aminocinnamate (8.62 g), Compound 3a (10.3 g, 62%) was obtained as a yellow solid in the same manner as Compound 1b was obtained.

$^1$H-NMR (CDCl$_3$) δ7.93 (2H, s), 7.84-7.83 (2H, m), 7.71 (2H, d, J=8.4 Hz), 7.64 (1H, s), 7.56 (2H, d, J=8.4 Hz), 6.39 (1H, d, J=15.9 Hz), 4.26 (2H, q, J=7.0 Hz), 1.34 (3H, t, J=7.0 Hz), 0.32 (18H, s); FAB-LRMS m/z 440 (MH$^+$).

4-[[3,5-Bis(trimethylsilyl)benzoyl]amino]cinnamic acid (3)

Using Compound 3a (10.7 g) and a 2N sodium hydroxide aqueous solution (234 ml), Crude Compound 3 (9.3 g) was obtained as an opalescent solid in the same manner as Compound 1 was obtained. Using Crude Compound 3 (600 mg), butyl acetate (7.2 ml) and heptane (1.8 ml), recrystallization was carried out to obtain Compound 3 (480 mg, 78%) as a white solid.

$^1$H-NMR (DMSO-d$_6$) δ12.4 (1H, brs), 10.4 (1H, s), 8.02 (2H, s), 7.85-7.82 (3H, m), 7.70 (2H, d, J=8.6 Hz), 7.57 (2H, d, J=15.9 Hz), 6.47 (2H, d, J=15.9 Hz), 0.31 (18H, s); FAB-LRMS m/z 412 (MH$^+$); Anal. Calcd for C$_{22}$H$_{29}$NO$_3$Si$_2$: C, 64.19; H, 7.10; N, 3.40. Found: C, 63.85; H, 7.13; N, 3.47. Melting point: 257.8 to 259.8° C. IR (cm$^{-1}$): 1687.1, 1628.1, 1593.0, 1526.6, 1512.3, 1320.6, 1290.1, 1188.7, 1178.8, 833.9, 665.8.

Formula 20

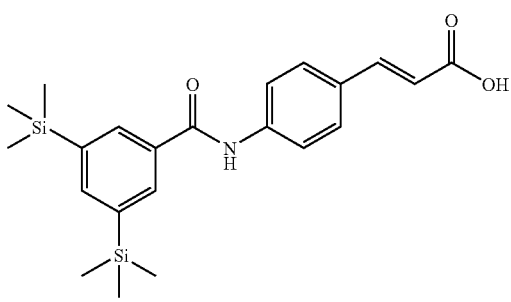

Example 4

3-[4-[[3,5-Bis(trimethylsilyl)benzoyl]amino]phenyl]propanoic acid (4)

Compound 3 (10 mg) was dissolved in methanol (1 ml), and a catalytic amount of palladium carbon was added thereto. The obtained mixture was stirred in a hydrogen atmosphere at room temperature for 5 hours. After the reaction was over, the reaction mixture was filtered through Celite, and the filtrate was purified by silica gel column chromatography to obtain Compound 4 (8 mg, 80%) as a white solid.

$^1$H-NMR (DMSO-d$_6$) δ10.17 (1H, s), 8.00 (2H, s), 7.79 (1H, s), 7.62 (2H, d, J=8.4 Hz), 7.20 (2H, d, J=8.4 Hz), 2.79 (2H, t, J=7.6 Hz), 2.50 (2H, t, J=7.5 Hz), 0.29 (18H, s); FAB-LRMS m/z 414 (MH$^+$).

Formula 21

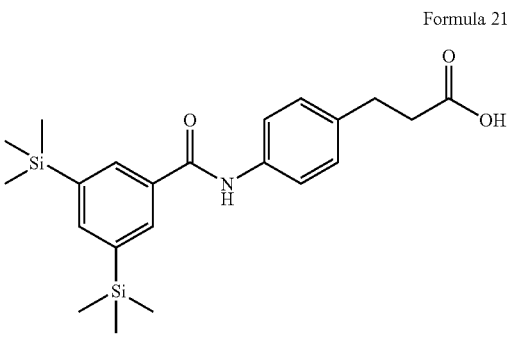

Example 5

(E)-n-Butyl 3-(2-methyl-4-nitrophenyl)-2-butenoate (5a)

A 0.28 mM palladium acetate solution (3.28 ml) was added to N-methylpyrrolidone (7 ml) solution of 2-bromo-5-nitrotoluene (1 g) and sodium acetate trihydrate (417 mg) in an argon atmosphere. The mixture was warmed to 120° C., and n-butyl acrylate (923 μl) was added thereto. The obtained mixture was stirred at 135° C. for 2 hours. A 0.28 mM palladium acetate solution (3.28 ml) and n-butyl acrylate (396 μl) were further added thereto, and the mixture was stirred for 4 hours. Subsequently, sodium acetate (265 mg) was added, and the mixture was further stirred for 1 hour. After the reaction was over, water (30 ml) was added to the resulting reaction mixture, and the mixture was separated with toluene and water. The organic layer was washed three times with water and once with a saturated sodium chloride solution, and then dried over anhydrous sodium sulfate. After the solvent was distilled off, the obtained residue was isolated and purified by silica gel column chromatography (n-hexane to ethyl acetate=8:1) to obtain Compound 5a (1.05 g, 86%).

$^1$H-NMR (CDCl$_3$) 8.08-8.04 (1H, m), 7.92 (1H, d, J=15.9 Hz), 7.67 (1H, d, J=8.6 Hz) 7.27-7.18 (1H, m), 6.40 (1H, d, J=15.9 Hz), 4.24 (2H, t, J=6.8 Hz), 2.53 (3H, s), 1.75-1.60 (2H, m), 1.52-1.35 (2H, m), 0.97 (3H, t, J=7.6 Hz).

(E)-n-Butyl 3-(2-methyl-4-aminophenyl)-2-butenoate (5b)

Compound 5a (1.05 g), iron powder (1.11 g), and ammonium chloride (0.32 g) were added to a mixed solution of tetrahydrofuran (4 ml), methanol (4 ml), and water (4 ml).

The mixture was stirred at 60° C. for 2 hours. The same amount of iron powder and ammonium chlorides were further added thereto, and the obtained mixture was stirred at 70° C. for 1 hour. After the reaction mixture was allowed to cool, and filtered, insoluble substances were filtered through Celite. The filtrate was condensed under reduced pressure to give Compound 5b (939 mg).

$^1$H-NMR (CDCl$_3$) 7.89 (1H, d, J=15.9 Hz), 7.43 (1H, d, J=8.1 Hz) 6.52-6.49 (2H, m), 6.20 (1H, d, J=15.7 Hz), 4.19 (2H, t, J=6.5 Hz), 3.85 (2H, brs), 2.36 (3H, s), 1.75-1.58 (2H, m), 1.50-1.35 (2H, m), 0.96 (3H, t, J=7.3 Hz).

(E)-n-Butyl 3-[4-[[3,5-bis(trimethylsilyl)benzoyl]amino]-2-methylphenyl]-2-butenoate (5c)

BTMB (1.42 g), 1-ethyl-3-(3-dimethylaminopropyl)carbodiimide hydrochloride (hereinafter referred to as "EDC"; 1.33 g), 1-hydroxybenzotriazole (hereinafter referred to as "HOBt"; 936 mg), and N,N-dimethylaminopyridine (847 mg) were dissolved in DMF (15 ml). Subsequently, a DMF (8 ml) solution of Compound 5b (939 mg) was added thereto, and the obtained mixture was stirred at room temperature for 18 hours and at 50° C. for 3 hours. After the reaction was over, the reaction mixture was allowed to cool, and water was added thereto. The mixture was separated with ethyl acetate and water. The organic layer was sequentially washed twice with a 0.1 N hydrochloric acid aqueous solution, twice with a saturated sodium-bicarbonate aqueous solution, and once with a saturated sodium chloride solution, and then dried over sodium sulfate. The solvent was distilled off under reduced pressure, and the obtained residue was isolated and purified by silica gel column chromatography (n-hexane to ethyl acetate=8:1) to obtain Compound 5c (1.21 g, 47%).

$^1$H-NMR (CDCl$_3$) δ7.94 (1H, d, J=15.9 Hz), 7.93 (2H, m), 7.83-7.78 (2H, m), 7.59-7.55 (3H, m), 6.35 (1H, d, J=15.9 Hz), 4.22 (2H, t, J=6.5 Hz), 2.47 (3H, s), 1.73-1.65 (2H, m), 1.55-1.40 (2H, m), 0.97 (3H, t, J=7.6 Hz), 0.33 (18H, s); FAB-LRMS m/z 482 (MH$^+$).

(E)-3-[4-[[3,5-Bis(trimethylsilyl)benzoyl]amino]-2-methylphenyl]-2-butenoic acid (5)

Compound 5c (304 mg) was dissolved in tetrahydrofuran (12 ml) and a 4.4% potassium hydroxide solution (8 ml) was added to the obtained mixture. The mixture was stirred at room temperature for 12 hours, and was further stirred under heating at 50° C. for 3 hours. The reaction mixture was allowed to cool, and a 2N hydrochloric acid aqueous solution was added thereto. The mixture was separated with ethyl acetate and water. The organic layer was sequentially washed once with a saturated sodium bicarbonate aqueous solution and once with a saturated sodium chloride solution, and then dried over sodium sulfate. The solvent was distilled off under reduced pressure, and the obtained residue was recrystallized with a mixed solvent of diethyl ether and n-hexane to obtain Compound 5 (164 mg, 61%).

$^1$H-NMR (CDCl$_3$) δ7.98 (1H, J=15.7 Hz), 7.87 (2H, d, J=1.1 Hz), 7.84-7.82 (2H, m), 7.62-7.60 (3H, m), 6.30 (1H, d, J=15.9 Hz), 2.49 (3H, s), 0.33 (18H, s); FAB-LRMS m/z 426 (MH$^+$).

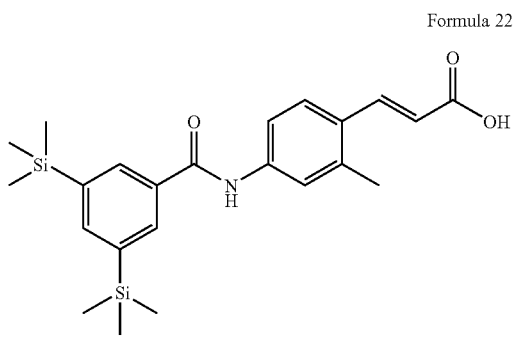

Formula 22

Example 6

(E)-Methyl 3-(4-nitrophenyl)-2-butenoate (6a)

18-Crown-6 (41.6 g) was added to a toluene (484 ml) solution of trimethyl phosphonoacetate (22.6 ml) in a nitrogen atmosphere. An 11% potassium hexamethyldisilazide (hereinafter referred to as "KHMDS")/toluene solution (315 ml) was added thereto, and the obtained mixture was stirred for 1 hour. Under ice-cooling, 4-nitroacetophenone (20 g) was added thereto, and the mixture was stirred for 1 hour. After the reaction was over, the reaction was stopped with a saturated ammonium chloride solution. The reaction mixture was separated with ethyl acetate and water. The organic layer was washed three times with water and once with a saturated sodium chloride solution, and then dried over anhydrous sodium sulfate. After the solvent was distilled off, the residue was suspended in methanol (40 ml) and stirred. The precipitated solid was filtered off and washed with cold methanol. Thus, Compound 6a (12.4 g, 46%) was obtained as an opalescent solid.

$^1$H-NMR (CDCl$_3$) δ8.24 (2H, d, J=8.8 Hz), 7.61 (2H, d, J=8.8 Hz), 6.19 (1H, s), 3.79 (3H, s), 2.59 (3H, s); FAB-LRMS m/z 222 (MH$^+$).

(E)-Methyl 3-(4-aminophenyl)-2-butenoate (6b)

Compound 6a (31.7 g), iron powder (41.1 g), ammonium chloride (18.1 g), and water (173 ml) were added to a mixed solution of tetrahydrofuran (280 ml) and methanol (280 ml) in a nitrogen atmosphere. The mixture was stirred at 70° C. for 1 hour. After the reaction mixture was allowed to cool, and filtered, the filtrate was separated with ethyl acetate and water. The organic layer was washed once with water and once with a saturated sodium chloride solution, and then dried over anhydrous sodium sulfate. The solvent was distilled off, and as a result, Compound 6b (25.7 g, 94%) was obtained as an orange solid.

$^1$H-NMR (CDCl$_3$) δ7.35 (2H, d, J=8.4 Hz), 6.66 (2H, d, J=8.4 Hz), 6.10 (1H, s), 3.84 (2H, brs), 3.73 (3H, s), 2.55 (3H, s); FAB-LRMS (negative) m/z 190 (M-H)$^-$.

(E)-Methyl 3-[4-[[3,5-bis(trimethylsilyl)benzoyl]amino]phenyl]-2-butenoate (6c)

EDC (31.3 g), HOBt (22 g), and 4-dimethylaminopyridine (19.9 g) were added to a DMF (538 ml) solution of BTMB (24 g) in a nitrogen atmosphere, and the mixture was stirred overnight. The mixture was separated with water and a mixed solution of ethyl acetate and toluene. The organic layer was washed three times with water and once with a saturated sodium chloride solution, and then dried over anhydrous sodium sulfate. The solvent was distilled off, and the residue was suspended in methanol (120 ml) and stirred. The precipitated solid was filtered off and washed with cold methanol. Thus, Compound 6c (44.5 g, 81%) was obtained as an opalescent solid.

$^1$H-NMR (CDCl$_3$) δ7.94 (2H, s), 7.84 (2H, d, J=6.8 Hz), 7.69 (2H, d, J=8.4 Hz), 7.52 (2H, d, J=8.4 Hz), 3.74 (3H, s), 2.59 (3H, s), 0.32 (18H, s); FAB-LRMS (negative) m/z 438 (M-H)$^-$.

(E)-3-[4-[[3,5-Bis(trimethylsilyl)benzoyl]amino]phenyl]-2-butenoic acid (6)

Using Compound 6c (39.2 g) and a 2N sodium hydroxide aqueous solution (134 ml), a solid reactant was obtained in the same manner as Compound 1 was obtained. The obtained solid was recrystallized three times using tert-butylmethyl ether and n-heptane to obtain Compound 6 (19.2 g, 50%) as a white solid.

$^1$H-NMR (CDCl$_3$) δ7.94 (2H, s), 7.83 (2H, s), 7.71 (2H, d, J=8.4 Hz), 7.56 (2H, d, J=8.4 Hz), 6.22 (1H, s), 2.62 (3H, s), 0.33 (18H, s); FAB-LRMS (negative) m/z 424 (M-H)$^-$. Melting point: 222.9 to 225.4° C. IR (cm$^{-1}$): 1694.5, 1644.2, 1629.6, 1595.5, 1323.3, 1248.0, 1214.2, 859.2, 832.8, 754.2, 683.8.

Formula 23

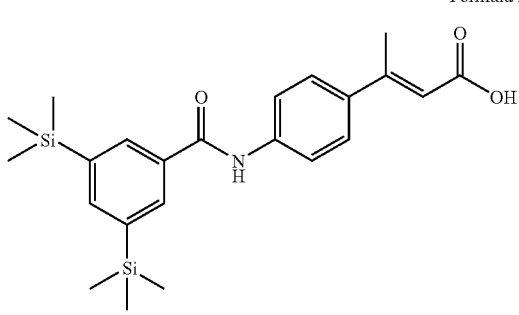

Example 7

3-[4-[[3,5-Bis(trimethylsilyl)benzoyl]amino]-2-fluorophenyl]propanoic acid (7)

Compound 2 (160 mg) was dissolved in a mixed solution of tetrahydrofuran (0.59 ml) and methanol (0.59 ml). Palladium carbon (4.4 mg) was added thereto, and the mixture was stirred in a hydrogen atmosphere for 4.5 hours. After the reaction was over, the reaction mixture was filtered through Celite. The filtrate was condensed and recrystallized with dichloromethane and n-hexane to obtain Compound 7 (122 mg, 76%) as a white solid.

$^1$H-NMR (DMSO-d$_6$) δ10.35 (1H, s), 8.00 (2H, s), 7.82 (2H, s), 7.67 (2H, d, J=10.5 Hz), 7.44 (2H, d, J=10.5 Hz), 7.28 (1H, t, J=8.6 Hz), 2.82 (2H, t, J=7.6 Hz), 2.52-2.49 (2H, m), 0.30 (18H, s); FAB-LRMS (negative) m/z 430 (M-H)$^-$.

Formula 24

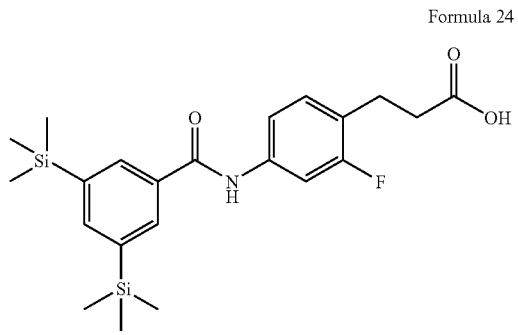

Example 8

Ethyl 4-amino-2-chlorocinnamate (8a)

Using 4-bromo-3-chloroaniline (5.0 g), Compound 8a (5.43 g, 99%) was obtained as a yellow solid in the same manner as Compound 2a was obtained.

$^1$H-NMR (CDCl$_3$) δ8.01 (1H, d, J=15.9 Hz), 7.45 (1H, d, J=8.6 Hz), 6.69 (1H, d, J=2.4 Hz), 6.54 (1H, dd, J=2.4 Hz, J=8.6 Hz), 6.24 (1H, d, J=15.9 Hz), 4.25 (2H, q, J=7.1 Hz), 3.99 (2H, brs), 1.33 (3H, t, J=7.1 Hz); FAB-LRMS (negative) m/z 224 (M-H)$^-$.

Ethyl 4-[[3,5-bis(trimethylsilyl)benzoyl]amino]-2-chlorocinnamate (8b)

Using BTMB (1.5 g) and Compound 8a (1.27 g), Compound 8b (1.42 g, 53%) was obtained as a light yellow solid in the same manner as Compound 1a was obtained.

$^1$H-NMR (CDCl$_3$) δ8.06 (1H, d, J=15.9 Hz), 7.92 (2H, s), 7.87 (1H, d, J=1.9 Hz), 7.84-7.83 (2H, m), 7.65 (1H, d, J=8.5 Hz), 7.59 (1H, dd, J=1.9 Hz, J=8.5 Hz), 6.41 (1H, d, J=15.9 Hz), 4.28 (2H, q, J=7.0 Hz), 1.35 (3H, t, J=7.0 Hz), 0.33 (18H, s); FAB-LRMS (negative) m/z 472 (M-H)$^-$.

4-[[3,5-Bis(trimethylsilyl)benzoyl]amino]-2-chlorocinnamic acid (8)

Using Compound 8b (1.42 g) and a 1N sodium hydroxide aqueous solution (15 ml), the aforementioned compound (1.12 g, 91%) was obtained as a white solid in the same manner as Compound 1 was obtained.

$^1$H-NMR (DMSO-d$_6$) δ10.54 (1H, s), 8.06 (1H, d, J=2.2 Hz), 8.02 (2H, s), 7.97 (1H, d, J=8.6 Hz), 7.85 (1H, d, J=15.8 Hz), 7.84-7.83 (1H, m), 7.78 (1H, dd, J=2.2 Hz, J=8.6 Hz), 6.57 (1H, d, J=15.8 Hz), 0.31 (18H, s); FAB-LRMS (negative) m/z 444 (M-H)$^-$.

Formula 25

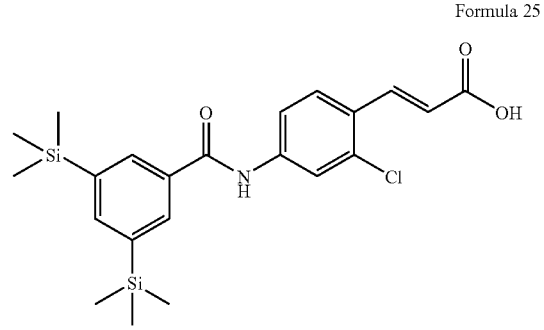

Example 9

(E)-Ethyl 3-(4-amino-3-fluorophenyl)-2-butenoate hydrochloride salt (9a)

A mixture of 4-bromo-2-fluoroaniline (5.0 g), ethyl crotonate (5.45 ml), palladium acetate (296 mg), tris(2-methylphenyl)phosphine (2.0 g), and triethylamine (30.2 ml) was stirred in a nitrogen atmosphere at 104° C. for 59 hours. The reaction mixture was filtered through Celite, and the filtrate was condensed. The obtained residue was separated with toluene and water. The organic layer was washed with a saturated sodium chloride solution, and then dried over anhydrous sodium sulfate. The solvent was distilled off, and silica gel (11 g) and toluene (15 ml) were added to the residue. The mixture was passed through a short column of silica gel (5 g) and eluted with toluene (140 ml). The resulting eluates were combined, and the solvent was distilled off. The residue was dissolved in toluene (40 ml) again, and 4N hydrochloric acid/ethyl acetate (8 ml) was added to the obtained mixture. The produced solid was filtered off and washed with toluene. Thus, Compound 9a (4.78 g, 70%) was obtained as a solid.

$^1$H-NMR (DMSO-d$_6$) δ7.32 (1H, dd, J=2.0 Hz, J=13.4 Hz), 7.22 (1H, dd, J=2.1 Hz, J=8.4 Hz), 6.80 (1H, t, J=8.9 Hz), 6.07 (1H, d, J=1.3 Hz), 4.09 (2H, q, J=7.1 Hz), 2.39 (3H, s), 1.11 (3H, t, J=7.1 Hz).

(E)-Ethyl 3-[4-[[3,5-bis(trimethylsilyl)benzoyl]amino]-3-fluorophenyl]-2-butenoate (9b)

Pyridine (272 μl) was added to a mixture of BTMB (400 mg), Compound 9a (483 mg), and acetonitrile (3 ml) in a nitrogen atmosphere. Under ice-cooling, phosphorus oxychloride (74.1 μl) was added to the mixture and stirred at a bath temperature of 95° C. for 2 hours. After ice-cooling the reaction mixture, water was added and extracted with ethyl acetate. The organic layer was washed once with a mixture of sodium bicarbonate solution and sodium chloride solution and once with a saturated sodium chloride solution, and then dried over anhydrous sodium sulfate. The solvent was distilled off, and the obtained residue was purified by silica gel column chromatography (17% ethyl acetate/n-hexane) to give Compound 9b (421 mg], 59%) as a light yellow solid.

$^1$H-NMR (DMSO-d$_6$) δ10.2 (1H, s), 8.06 (2H, s), 7.82 (1H, s), 7.63 (1H, t, J=8.5 Hz), 7.45-7.60 (2H, m), 6.25 (1H, s), 4.15 (2H, q, J=7.1 Hz), 2.52 (3H, s), 1.24 (3H, t, J=7.1 Hz), 0.29 (18H, s).

(E)-3-[4-[[3,5-Bis(trimethylsilyl)benzoyl]amino]-3-fluorophenyl]-2-butenoic acid (9)

A mixture of Compound 9b (720 mg) and ethanol (5.9 ml) was heated to 50° C. A 1N sodium hydroxide aqueous solution (3.94 ml) was added thereto, and the mixture was stirred at 50° C. for 1.5 hours. The reaction mixture was ice-cooled, and a 6N hydrochloric acid aqueous solution (660 μl) was added thereto. The obtained mixture was stirred at room temperature for 3 hours. The precipitated solid was filtered off and crystallized with a mixed solvent of tert-butylmethylether/n-heptane (1:4). The precipitated solid was filtered off, and as a result, Compound 9 (171 mg, 49%) was obtained as a white solid.

$^1$H-NMR (DMSO-d$_6$) δ10.2 (1H, s), 8.07 (2H, s), 7.82 (1H, s), 7.66 (1H, d, J=8.3 Hz), 7.43-7.56 (2H, m), 6.19 (1H, s), 2.49 (3H, s), 0.30 (18H, s); FAB-LRMS (negative) m/z 442 (M-H)$^-$.

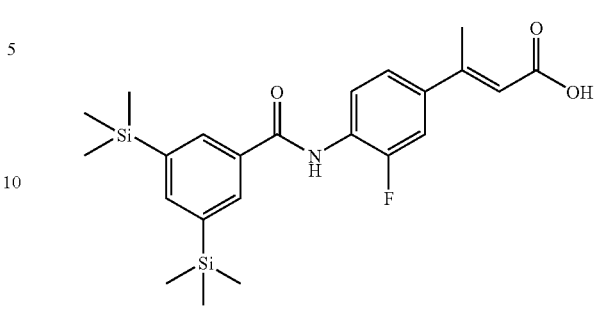

Formula 26

Example 10

(E)-Ethyl 3-(4-amino-2,5-difluorophenyl)-2-butenoate (10a)

A mixture of 4-bromo-2,5-difluoroaniline (5.0 g), ethyl crotonate (4.98 ml), palladium acetate (54.0 mg), tris(2-methylphenyl)phosphine (442 mg), and triethylamine (33.4 ml) was stirred at 110° C. in a nitrogen atmosphere for 48 hours. The reaction mixture was filtered through Celite, and the filtrate was concentrated. The obtained residue was separated with ethyl acetate and water. The organic layer was washed with a saturated sodium chloride solution, and then dried over anhydrous sodium sulfate. The solvent was distilled off, and the residue was purified by column chromatography (5% ethyl acetate/n-hexane) to give Compound 10a (1.69 g, 29%) as a brown solid.

$^1$H-NMR (CDCl$_3$) δ6.93 (1H, dd, J=7.0 Hz, J=11.9 Hz), 6.45 (1H, dd, J=7.0 Hz, J=11.9 Hz), 5.98 (1H, s), 4.18 (2H, q, J=7.0 Hz), 3.92 (2H, brs), 2.46 (3H, s), 1.28 (2H, t, J=7.0 Hz); FAB-LRMS (negative) m/z 240 (M-H)$^-$.

(E)-Ethyl 3-[4-[[3,5-bis(trimethylsilyl)benzoyl]amino]-2,5-difluorophenyl]-2-butenoate (10b)

BTMB (800 mg) and Compound 10a (869 mg) were reacted in the same manner as Compound 2b was synthesized. After the reaction was over, the reaction mixture was separated with ethyl acetate and water. The organic layer was washed once with water and once with a saturated sodium chloride solution, and then dried over anhydrous sodium sulfate. The solvent was distilled off, and the residue was purified by column chromatography (5% ethyl acetate/n-hexane) to obtain Compound 10b (674 mg, 46%) as a light yellow solid.

$^1$H-NMR (CDCl$_3$) δ8.38 (2H, dd, J=6.8 Hz, J=11.3 Hz), 8.08 (1H, brs), 7.94 (2H, s), 7.85 (1H, s), 7.10 (2H, dd, J=6.8 Hz, J=11.3 Hz), 6.05 (1H, s), 4.22 (2H, q, J=7.0 Hz), 2.53 (3H, s), 1.32 (3H, t, J=7.0 Hz), 0.33 (18H, s); FAB-LRMS (negative) m/z 488 (M-H)$^-$.

(E)-3-[4-[[3,5-Bis(trimethylsilyl)benzoyl]amino]-2,5-difluorophenyl]-2-butenoic acid (10)

Using Compound 10b and a 1N sodium hydroxide aqueous solution, Compound 10 (400 mg, 65%) was obtained as a white solid in the same manner as Compound 2 was synthesized.

$^1$H-NMR (DMSO-$d_6$) δ10.32 (1H, s), 8.06 (2H, s), 7.84 (1H, s), 7.70-7.64 (2H, m), 7.50-7.43 (2H, m), 6.02 (1H, s), 2.49 (3H, s), 0.31 (18H, s); FAB-LRMS (negative) m/z 460 (M-H)$^-$.

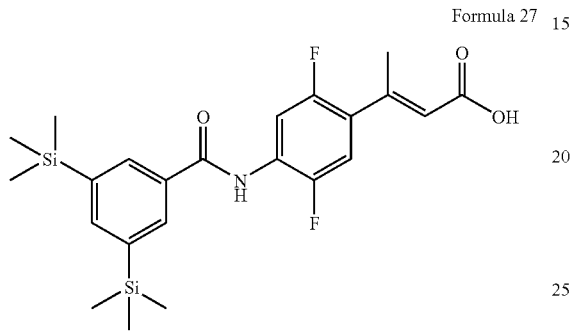

Formula 27

Example 11

(E)-Ethyl 3-(4-amino-2-fluorophenyl)-2-butenoate (11a)

Using 4-bromo-3-fluoroaniline (10.0 g) and ethyl crotonate (10.9 ml), Compound 11a (2.01 g, 17%) was obtained as a brown solid in the same manner as Compound 10a was synthesized.

$^1$H-NMR (CDCl$_3$) δ7.10 (1H, t, J=8.4 Hz), 6.44-6.34 (2H, m), 5.99 (1H, s), 4.20 (2H, q, J=7.0 Hz), 3.88 (2H, brs), 2.50 (3H, s), 1.30 (3H, t, J=7.0 Hz); FAB-LRMS (negative) m/z 222 (M-H)$^-$.

(E)-Ethyl 3-[4-[[3,5-bis(trimethylsilyl)benzoyl]amino]-2-fluorophenyl]-2-butenoate (11b)

Using BTMB (1.0 g) and Compound 11a (1.01 g), Compound 11b (739 mg, 42%) was obtained as a light yellow solid in the same manner as Compound 10b was synthesized.

$^1$H-NMR (CDCl$_3$) δ7.93 (2H, s), 7.87 (1H, s), 7.84 (2H, t, J=1.4 Hz), 7.68 (1H, d, J=13.0 Hz), 7.31-7.29 (2H, m), 6.04 (1H, s), 4.22 (2H, q, J=7.0 Hz), 2.54 (3H, s), 1.32 (3H, t, J=7.0 Hz), 0.33 (18H, s); FAB-LRMS m/z 472 (MH$^+$).

(E)-3-[4-[[3,5-Bis(trimethylsilyl)benzoyl]amino]-2-fluorophenyl]-2-butenoic acid (11)

Using Compound 11b (719 mg) and a 1N sodium hydroxide aqueous solution (7.63 ml), Compound 11 (550 mg, 81%) was obtained as a white solid in the same manner as Compound 1 was synthesized.

$^1$H-NMR (DMSO-$d_6$) δ10.5 (1H, s), 8.01 (2H, s), 7.84-7.77 (2H, m), 7.58 (1H, d, J=8.6 Hz), 7.45 (1H, t, J=8.6 Hz), 5.97 (1H, s), 2.51 (3H, s), 0.31 (18H, s); FAB-LRMS (negative) m/z 442 (M-H)$^-$.

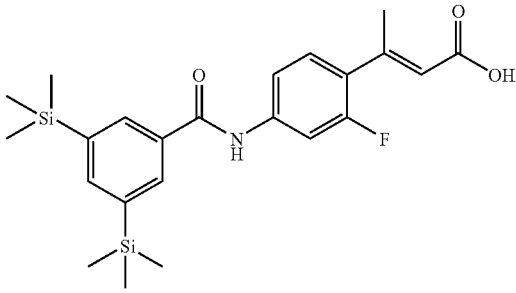

Formula 28

Example 12

(E)-Ethyl 3-(4-amino-2-chlorophenyl)-2-butenoate (12a)

Using 4-bromo-3-chloroaniline (10.0 g) and ethyl crotonate (10.0 ml), Compound 12a (3.56 g, 31%) was obtained as a brown solid in the same manner as Compound 10a was synthesized.

$^1$H-NMR (CDCl$_3$) δ6.96 (1H, d, J=8.1 Hz), 6.70 (1H, d, J=2.4 Hz), 6.49 (1H, dd, J=2.4 Hz, J=8.1 Hz), 5.82 (1H, s), 4.20 (2H, t, J=7.0 Hz), 3.78 (2H, brs), 2.50 (3H, s) 1.30 (3H, t, J=7.0 Hz); FAB-LRMS (negative) m/z 238 (M-H)$^-$.

(E)-3-[4-[[3,5-Bis(trimethylsilyl)benzoyl]amino]-2-chlorophenyl]-2-butenoic acid (12)

Using BTMB (2.0 g) and Compound 12a (2.16 g), 1.91 g of an ester body of Compound 12 was obtained as a light yellow solid in the same manner as Compound 10b was synthesized, except that purification was not conducted. Additionally, using the ester body (1.9 g) of Compound 12 and a 1N sodium hydroxide aqueous solution (19.5 ml), Compound 12 (1.36 g, 76%) was obtained as a white solid in the same manner as Compound 1 was synthesized.

$^1$H-NMR (CDCl$_3$) δ7.93 (1H, s), 7.84-7.81 (3H, m), 7.57 (1H, d, J=10.3 Hz), 7.20 (1H, d, J=8.4 Hz), 5.91 (1H, s), 2.52 (3H, s), 0.32 (18H, s); FAB-LRMS (negative) m/z 460 (MH$^+$).

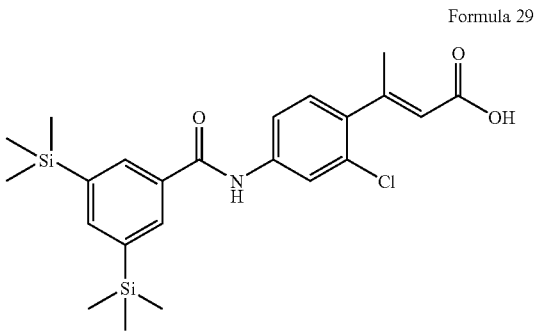

Formula 29

Example 13

(E)-Ethyl 3-(4-aminophenyl)-2-methylacrylate (13a)

4-Nitrobenzaldehyde (4.20 g) and (carbetoxyethylidene) triphenylphosphorane (10 g) were dissolved in toluene (36 ml), and the obtained mixture was stirred overnight under reflux conditions. After the obtained reaction mixture was allowed to cool, N-pentane (50 ml) was added thereto, and the produced white precipitate was filtered off. The filtrate was concentrated, and N-pentane (70 ml) was added to the residue. Then, ultrasonic waves were applied to the mixture. The produced precipitate was filtered off and dried under reduced pressure to obtain crude (E)-ethyl 3-(4-nitrophenyl)-2-methylacrylate as a yellow powder.

The obtained ethyl 3-(4-nitrophenyl)-2-methylacrylate (3.5 g) was dissolved in a mixed solvent of water (75 ml), methanol (75 ml), and THF (75 ml). Ammonium chloride (3.05 g) and iron powder (4.2 g) were added thereto, and the obtained mixture was stirred at 50° C. for 4 hours. The iron powder was filtered, and the solvent was distilled off under reduced pressure. Methanol was added to the obtained residue, and insoluble substances were filtered off. The filtrate was separated with ethyl acetate and water. The organic layer was washed with a saturated sodium chloride solution, and then dried over anhydrous sodium sulfate. The solvent was distilled off, and the residue was purified by silica gel column chromatography (3% chloroform/methanol) to obtain Compound 13a (1.8 g, 32%) as an orange liquid.

$^1$H-NMR (DMSO-$d_6$) δ7.44 (1H, s), 7.22 (2H, d, J=8.1 Hz), 6.58 (1H, d, J=8.1 Hz), 5.60 (2H, brs), 4.14 (2H, q, J=7.1 Hz), 2.04 (3H, s), 1.23 (3H, t, J=7.1 Hz); FAB-LRMS (negative) m/z 204 (M-H)$^-$.

(E)-Ethyl 3-[4-[[3,5-bis(trimethylsilyl)benzoyl]amino]phenyl]-2-methylacrylate (13b)

Using BTMB (1.95 g) and Compound 13a (1.8 g), Compound 13b (910 mg, 27%) was obtained as a yellow solid in the same manner as Compound 2b was synthesized.

$^1$H-NMR (CDCl$_3$) δ10.4 (1H, s), 8.01 (2H, s), 7.84 (2H, d, 8.5 Hz), 7.82 (1H, s), 7.59 (1H, s), 7.52 (2H, d, J=8.5 Hz), 4.21 (2H, q, J=7.1 Hz), 2.10 (3H, s), 1.27 (3H, t, J=7.1 Hz), 0.31 (18H, s); FAB-LRMS (negative) m/z 452 (M-H)$^-$.

(E)-3-[4-[[3,5-Bis(trimethylsilyl)benzoyl]amino]phenyl]-2-methylacrylic acid (13)

Using Compound 13b (900 mg) and a 2N sodium hydroxide aqueous solution (10 ml), Compound 13 (630 mg) was obtained as a white solid in the same manner as Compound 2 was synthesized.

$^1$H-NMR (DMSO-$d_6$) δ12.4 (1H, brs), 10.4 (1H, s), 8.02 (2H, s), 7.83 (3H, m), 7.58 (1H, s), 7.51 (2H, d, J=8.5 Hz), 2.07 (3H, s), 0.30 (18H, s); FAB-LRMS (negative) m/z 424 (M-H)$^-$.

Formula 30

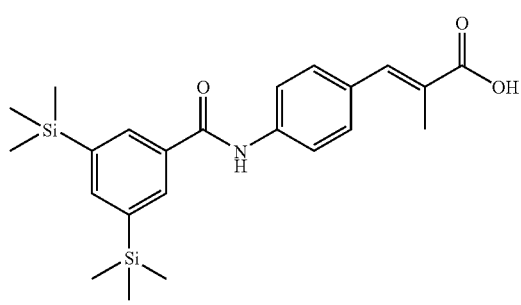

Example 14

N-Methoxy-N-methyl-4-nitro-2-fluorobenzamide (14a)

4-Nitro-2-fluorobenzoic acid (5.03 g) was dissolved in pyridine (60.0 ml), and N,O-dimethylhydroxylamine hydrochloride (7.95 g), HOBt (5.50 g), and EDC (7.79 g) were added thereto. The obtained mixture was stirred at 60° C. for 15 hours. After the reaction mixture was allowed to cool, the solvent was distilled off under reduced pressure. Water and ethyl acetate were added to the obtained residue, and extraction and washing were carried out. The organic layer was sequentially washed with a 1N hydrochloric acid aqueous solution, saturated sodium-bicarbonate aqueous solution, and saturated sodium chloride solution, and then dried over anhydrous sodium sulfate. The solvent was distilled off under reduced pressure. The residue was recrystallized with a mixed solvent of tert-butylmethylether and n-heptane to obtain Compound 14a (5.28 g, 85%) as an opalescent solid.

$^1$H-NMR (CDCl$_3$) δ8.01 (1H, dd, J=2.0 Hz, J=8.4 Hz), 7.98 (1H, dd, J=2.0 Hz, J=8.4 Hz), 7.60 (1H, dd, J=6.5 Hz, J=8.2 Hz), 3.51 (3H, s), 3.37 (3H, s); FAB-LRMS m/z 229 (MH$^+$).

4-Nitro-2-fluorobenzaldehyde (14b)

Compound 14a (860 mg) was dissolved in tetrahydrofuran (10.0 ml), and the reaction mixture was ice-cooled. Diisobutylaluminum hydride/toluene solution (0.98 mol/l, 5.0 ml) was added thereto, and the mixture was stirred under ice-cooling for 1 hour. After adding a 1N hydrochloric acid aqueous solution, the reaction mixture was returned to room temperature and extracted with ethyl acetate. The organic layer was washed with a 1N hydrochloric acid aqueous solution and saturated sodium-hydrogencarbonate aqueous solution, and then dried over anhydrous sodium sulfate. The solvent was distilled off under reduced pressure. The obtained residue was recrystallized with a mixed solvent of tert-butylmethylether and n-heptane to obtain Compound 14b (554 mg, 86%) as a white solid.

$^1$H-NMR (CDCl$_3$) δ10.45 (1H, s), 8.11 (3H, m); EI-LRMS m/z 169 (M$^+$).

(E)-Ethyl 3-(2-fluoro-4-nitrophenyl)-2-methylacrylate (14c)

Compound 14b (14.6 mg) was dissolved in toluene (132 ml), and (carbetoxyethylidene)triphenylphosphorane (46.9 g) was added thereto. The obtained mixture was stirred under heating at 120° C. for 2 hours. After the reaction mixture was allowed to cool, n-heptane was added thereto and stirred. The precipitated solid was filtered off, and the filtrate was concentrated under reduced pressure. The obtained residue was dissolved in methanol (125 ml), and purified water was added thereto. The precipitated solid was filtered off and then dried under reduced pressure. Thus, Compound 14c (17.3 g, 79%) was obtained as an opalescent solid.

$^1$H-NMR (CDCl$_3$) δ8.08 (1H, dd, J=2.1 Hz, J=8.6 Hz), 8.00 (1H, dd, J=2.1 Hz, J=9.7 Hz), 7.64 (1H, s), 7.52 (1H, t, J=8.6 Hz), 4.32 (2H, q, J=7.0 Hz), 2.05 (3H, s), 1.35 (3H, t, J=7.0 Hz); FAB-LRMS m/z 254 (MH$^+$).

(E)-Ethyl 3-(2-fluoro-4-aminophenyl)-2-methylacrylate (14d)

Compound 14c (17.3 g) was dissolved in tetrahydrofuran (180 ml) and methanol (180 ml), and iron powder (19.1 g) was added thereto. An ammonium chloride aqueous solution (1.67 mol/l, 110 ml) was added to the reaction mixture while refluxing under heating. The obtained mixture was refluxed under heating for 1 hour. After the mixture was allowed to cool, the iron powder was removed by Cerite filtration. Ethyl acetate and purified water were added to the filtrate, and extraction and washing were carried out. The organic layer was dried over anhydrous sodium sulfate, and the solvent was distilled off under reduced pressure. The obtained residue was recrystallized with n-heptane to obtain Compound 14d (13.0 g, 85%) as an opalescent solid.

$^1$H-NMR (CDCl$_3$) δ7.64 (1H, s), 7.24 (1H, dd, J=8.5 Hz, J=7.6 Hz), 6.45 (1H, dd, J=2.2 Hz, J=8.5 Hz), 6.39 (1H, dd, J=2.2 Hz, J=12.0 Hz), 4.26 (2H, q, J=7.1 Hz), 3.92 (2H, brs), 2.06 (3H, s), 1.34 (3H, t, J=7.1 Hz); FAB-LRMS m/z 222 (MH$^-$).

(E)-Ethyl 3-[4-[[3,5-bis(trimethylsilyl)benzoyl]amino]-2-fluorophenyl]-2-methylacrylate (14e)

Pyridine (4.28 ml) and Compound 14d (13.0 g) were added to an acetonitrile (113 ml) solution of BTMB (14.1 g) in a nitrogen atmosphere, and phosphorus oxychloride (3.60 ml) was added dropwise under ice-cooling. After the mixture was stirred while refluxing under heating for 1.5 hours, the mixture was allowed to cool. Water was added thereto and the mixture was stirred. The precipitated solid was filtered off, and a 1N hydrochloric acid aqueous solution and purified water was drizzled on to wash. The obtained solid was dried under reduced pressure, and then suspended and stirred in methanol (112 ml). After purified water was added thereto, the solid was filtered off and dried under reduced pressure. Thus, Compound 14e (18.9 g, 77%) was obtained as an opalescent solid.

$^1$H-NMR (CDCl$_3$) δ7.93 (2H, d, J=1.2 Hz), 7.86 (1H, brs), 7.84 (1H, t, J=1.2 Hz), 7.69-7.72 (2H, m), 7.38 (1H, dd, J=7.8 Hz, J=8.3 Hz), 7.33 (1H, dd, J=2.2 Hz, J=8.3 Hz), 4.28 (2H, q, J=7.1 Hz), 2.07 (3H, s), 1.36 (3H, t, J=7.1 Hz); FAB-LRMS m/z 472 (MH$^+$).

(E)-3-[4-[[3,5-Bis(trimethylsilyl)benzoyl]amino]-2-fluorophenyl]-2-methylacrylic acid (14)

Compound 14e (18.9 g) was dissolved in ethanol (302 ml), and a 2N sodium hydroxide aqueous solution (100 ml) was added thereto. The obtained mixture was stirred under heating at 50° C. for 2 hours. The reaction mixture was ice-cooled, and a 1N hydrochloric acid aqueous solution (300 ml) was added to neutralize the mixture. The precipitated solid was filtered off and dried under reduced pressure to obtain Crude Compound 14 (16.6 g) as a white solid. Crude Compound 14 (400 mg) was recrystallized with ethanol (4.0 ml) and purified water (4.0 ml) to obtain Compound 14 (344 mg, 86%) as a white solid.

$^1$H-NMR (DMSO-d$_6$) δ12.6 (1H, brs), 10.55 (1H, s), 8.01 (2H, d, J=0.8 Hz), 7.86-7.80 (2H, m), 7.64-7.51 (3H, m), 1.99 (3H, s), 0.31 (18H, s); FAB-LRMS m/z 444 (MH$^+$). Melting point: 213.4 to 215.2° C. IR (cm$^{-1}$): 1689.7, 1651.6, 1616.6, 1586.0, 1510.6, 1413.1, 1288.6, 1248.4, 1176.4, 1139.3, 996.1, 928.8, 836.9, 751.1, 688.7.

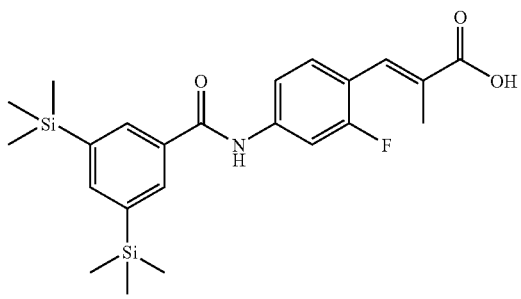

Formula 31

Example 15

Methyl 4-amino-2-fluorocinnamate (15a)

4-Bromo-3-fluoroaniline (20.0 g) was dissolved in a mixed solvent of DMF (64 ml) and N,N-diisopropylethylamine (64 ml). Methyl acrylate (28.3 ml), palladium acetate (1.18 g), and tris(2-methylphenyl)phosphine (11.2 g) were added thereto in a nitrogen atmosphere. The obtained mixture was stirred at a bath temperature of 120 to 129° C. for 26 hours. Toluene was added to the reaction mixture, and the mixture was filtered through Cerite. The Cerite was washed with a mixed solvent of DMF and toluene (1:1, 80 ml). The filtrates were combined and concentrated under reduced pressure. The obtained residue was separated with ethyl acetate and water. The organic layer was washed with a saturated sodium chloride solution, and then dried over anhydrous sodium sulfate. The solvent was distilled off, and toluene (70 ml) and n-heptane (10 ml) were added to the obtained residue. The precipitated solid was filtered off, and as a result, Compound 15a (3.74 g, 36%) was obtained as a yellow solid.

$^1$H-NMR (CDCl$_3$) δ7.72 (1H, d, J=16.2 Hz), 7.32 (1H, t, J=8.2 Hz), 6.44-6.33 (2H, m), 6.33 (1H, d, J=16.2 Hz), 4.04 (2H, brs), 3.78 (3H, s); FAB-LRMS (negative) m/z 194 (M-H)$^-$.

Methyl 4-[[3,5-bis(trimethylsilyl)benzoyl]amino]-2-fluorocinnamate (15)

BTMB (800 mg) was suspended in acetonitrile (6 ml), and pyridine (243 μl) and Compound 15a (726 mg) were added thereto. Phosphorus oxychloride (148 μl) was added dropwise thereto at 0° C. in a nitrogen atmosphere. The obtained mixture was stirred under reflux conditions for 4 hours. The reaction mixture was ice-cooled. Water (8.2 ml) was added thereto, and the mixture was stirred at room temperature for 2 hours. The precipitated powder was filtered off, washed with a 1N hydrochloric acid aqueous solution and water, and then dried. The obtained solid was suspended in methanol (7 ml), and the suspension was stirred at room temperature for 1 hour. Water (1.4 ml) was added thereto and a white solid was filtered off. As a result, Compound 15 (1.07 g, 80%) was obtained as a light yellow solid.

$^1$H-NMR (DMSO-d$_6$) δ10.60 (1H, s), 8.05 (2H, s), 7.91-7.81 (3H, m), 7.67 (1H, d, J=16.2 Hz), 7.59 (1H, dd, J=11.0 Hz, J=1.8 Hz), 6.61 (1H, d, J=16.2 Hz), 3.73 (3H, s), 0.29 (18H, s); FAB-LRMS m/z 444 (MH$^+$).

Formula 32

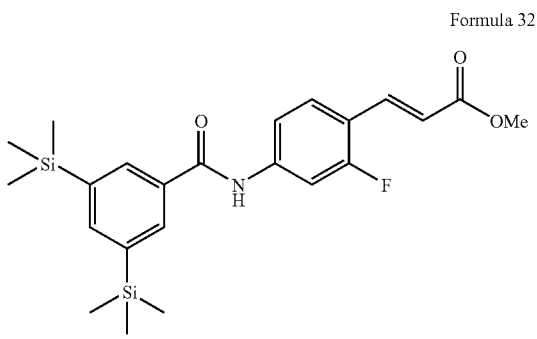

Example 16

3-[4-[[3,5-Bis(trimethylsilyl)benzoyl]amino]-2-fluoro-phenyl]-2-methylpropanoic acid (16)

Compound 14 (214 mg) was dissolved in tetrahydrofuran (4.0 ml) and methanol (4.0 ml), and a 10% palladium carbon catalyst (70.0 mg) was added thereto. The obtained mixture was stirred at room temperature in a hydrogen atmosphere for 6 hours. The catalyst was removed by Cerite filtration, and the solvent was distilled off from the filtrate under reduced pressure. As a result, Compound 16 (202 mg, 94%) was obtained as an opalescent solid.
$^1$H-NMR (CDCl$_3$) δ8.03 (1H, brs), 7.93 (2H, d, J=1.2 Hz), 7.80 (1H, t, J=1.2 Hz), 7.60 (1H, dd, J=1.6 Hz, J=12.0 Hz), 7.26-7.12 (2H, m), 3.03-2.93 (1H, m), 2.86-2.76 (2H, m), 1.22 (3H, d, J=6.6 Hz), 0.32 (18H, s); EI-LRMS m/z 445 (M$^+$)

Formula 33

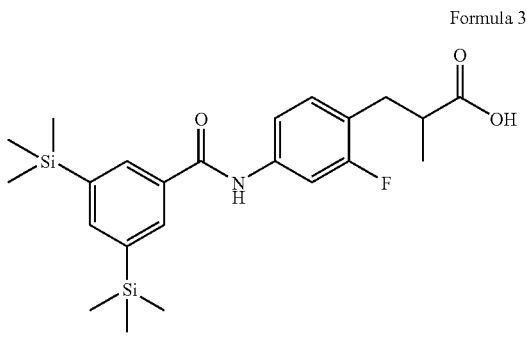

Example 17

Ethyl 4-[[3,5-bis(trimethylsilyl)benzoyl]amino]cinnamate (17a)

BTMB (300 mg) was dissolved in DMF (96 μl) and dimethyl sulfoxide (28.5 ml). Calcium carbonate (304 mg) and thionyl chloride (180 μl) were added thereto in a nitrogen atmosphere. After the obtained mixture was stirred at room temperature for 4 hours, the reaction mixture was filtered, and the solvent was distilled off. Tetrahydrofuran (3 ml) was added to the obtained residue, and in addition, 4-aminocinnamic acid ethyl ester (258 mg) and triethylamine (350 μl) were added in a nitrogen atmosphere. The obtained mixture was stirred at room temperature overnight. After the reaction was over, a saturated ammonium chloride solution and ethyl acetate were added to the reaction mixture. The organic layer was washed once with water and once with a saturated sodium chloride solution, and then dried over anhydrous sodium sulfate. The solvent was distilled off, and the residue was purified by neutral silica gel column chromatography (5% ethyl acetate/n-hexane) to obtain Compound 17a (293 mg, 59.2%) as a white foam material.
$^1$H-NMR (CDCl$_3$) δ7.94 (2H, s), 7.83 (2H, s), 7.11 (2H, d, J=8.6 Hz), 7.64 (1H, s), 7.56 (2H, d, J=8.6 Hz), 6.40 (1H, d, J=16.2 Hz), 4.27 (2H, q, J=7.0 Hz), 1.34 (3H, t, J=7.0 Hz), 0.33 (18H, s); FAB-LRMS m/z 440 (MH$^+$).

Ethyl 4-[[3,5-bis(trimethylsilyl)benzenecarbothioyl]amino]cinnamate (17b)

Compound 17a (293 mg) was dissolved in toluene (8.34 ml), and Lawesson's reagent (189 mg) was added thereto in a nitrogen atmosphere. The obtained mixture was stirred while refluxing under heating for 2 hours. The solvent was distilled off, and the residue was purified by neutral silica gel column chromatography (10% ethyl acetate/n-hexane) to obtain Compound 17b (319 mg, 76%) as a yellow foam material.
$^1$H-NMR (CDCl$_3$) δ9.02 (1H, brs), 7.87 (3H, brs), 7.77 (1H, brs), 7.70 (1H, brs), 7.64 (1H, brs), 7.61-7.58 (2H, m), 6.43 (1H, d, J=15.9 Hz), 4.27 (2H, q, J=7.0 Hz), 1.35 (3H, t, J=7.0 Hz), 0.31 (18H, s); FAB-LRMS (negative) m/z 454 (M-H)$^-$.

4-[[3,5-Bis(trimethylsilyl)benzenecarbothioyl]amino]cinnamic acid (17)

A 2N sodium hydroxide aqueous solution (6.99 ml) was added to an ethanol solution of Compound 17b (319 mg) in a nitrogen atmosphere. The obtained mixture was stirred at room temperature overnight. After the reaction was over, the reaction mixture was ice-cooled, and a 2N hydrochloric acid aqueous solution was added thereto. The precipitated solid was filtered off and recrystallized with a mixed solvent of n-hexane and ethyl acetate to obtain Compound 17 (183 mg, 61%) as a yellow solid.
$^1$H-NMR (DMSO-d$_6$) δ11.85 (1H, brs), 7.97-7.94 (2H, m), 7.86 (2H, s), 7.78-7.75 (3H, m), 7.60 (1H, d, J=15.9 Hz), 6.54 (1H, d, J=15.9 Hz), 0.30 (18H, s); FAB-LRMS m/z 428 (MH$^+$); mp 222° C. (decomp.).

Formula 34

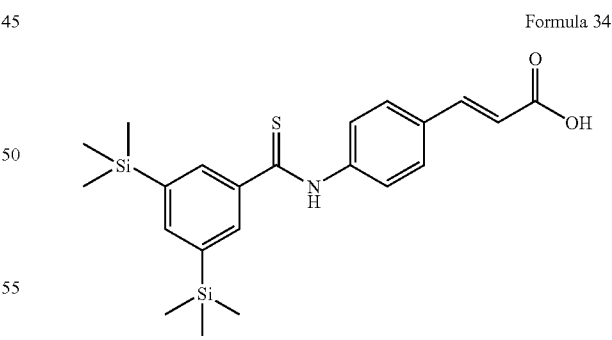

Example 18

(E)-Ethyl 3-[6-[[3,5-bis(trimethylsilyl)benzoyl]amino]pyridin-3-yl]acrylate (18a)

BTMB (500 mg) was suspended in acetonitrile (3.75 ml) in a nitrogen atmosphere. Pyridine (152 μl) and ethyl 3-(6-aminopyridine-3-yl)acrylate (431 mg) were added thereto, and phosphorus oxychloride (93.9 μl) was added dropwise under ice-cooling. The obtained mixture was stirred while refluxing under heating for 3.5 hours. After the reaction mixture was allowed to cool, water (5.1 ml) was added, and the mixture was stirred for 1 hour. The precipitated solid was filtered off. Diisopropyl alcohol (1.32 ml) was added thereto, and the mixture was stirred for 30 minutes. The solid was filtered off and washed with diisopropyl alcohol. As a result, Compound 18a (466 mg, 57%) was obtained as an opalescent solid.

$^1$H-NMR (CDCl$_3$) δ8.70 (1H, s), 8.47 (1H, d, J=8.6 Hz), 8.43 (1H, s), 8.00 (2H, s), 7.96 (1H, d, J=8.6 Hz), 7.85 (1H, s), 7.66 (1H, d, J=15.9 Hz), 6.46 (1H, d, J=15.9 Hz), 4.28 (2H, q, J=7.0 Hz), 1.35 (3H, t, J=7.0 Hz), 0.33 (18H, s); FAB-LRMS m/z 441 (MH$^+$).

(E)-Ethyl 3-[6-[[3,5-bis(trimethylsilyl)benzenecarbothioyl]amino]pyridin-3-yl]acrylate (18b)

Using Compound 18a (135 mg) and Lawesson's reagent (86.7 mg), Compound 18b (90.7 mg, 65%) was obtained as a yellow solid in the same manner as Compound 17b was synthesized.

$^1$H-NMR (CDCl$_3$) δ9.86 (1H, s), 9.28 (1H, d, J=8.6 Hz), 8.47 (1H, d, J=2.4 Hz), 7.97 (1H, dd, J=8.6 Hz, J=2.4 Hz), 7.90 (2H, s), 7.78 (1H, s), 7.66 (1H, d, J=16.2 Hz), 6.48 (1H, d, J=16.2 Hz), 4.29 (2H, q, J=7.0 Hz), 1.36 (3H, t, J=7.0 Hz), 0.33 (18H, s); FAB-LRMS (negative) m/z 455 (M-H)$^-$.

(E)-3-[6-[[3,5-Bis(trimethylsilyl)benzenecarbothioyl]amino]pyridin-3-yl]acrylic acid (18)

Using Compound 18b (90.7 mg) and a 2N sodium hydroxide aqueous solution (13.9 ml), Compound 18 (64.8 mg, 76%) was obtained as a yellow solid in the same manner as Compound 17 was synthesized.

$^1$H-NMR (DMSO-d$_6$) δ8.77 (1H, s), 8.48 (1H, brs), 8.29-8.25 (1H, m), 7.91 (2H, s), 7.75 (1H, s), 7.64 (1H, d, J=15.9 Hz), 6.68 (1H, d, J=15.9 Hz), 0.29 (18H, s); FAB-LRMS (negative) m/z 427 (M-H)$^-$; mp 270° C. (decomp.).

Formula 35

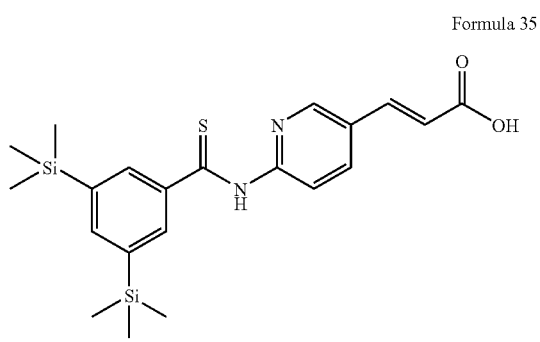

Example 19

(E)-Ethyl 3-(4-nitrophenyl)-2-butenoate (19a)

A toluene (90 ml) solution of 4-nitroacetophenone (2.0 g) and (carbethoxymethylidene)triphenylphosphorane (6.33 g) was stirred while refluxing under heating for 10 hours. After the solution was allowed to cool, the solvent was distilled off. The obtained residue was purified by column chromatography (6.25% ethyl acetate/n-hexane) to obtain Compound 19a (829 mg, 29%) as a white solid.

$^1$H-NMR (CDCl$_3$) δ8.24 (2H, d, J=9.2 Hz), 7.61 (2H, d, J=9.2 Hz), 6.18 (1H, s), 4.24 (2H, q, J=7.0 Hz), 2.59 (3H, s), 1.33 (3H, t, J=7.0 Hz); FAB-LRMS m/z 222 (MH$^+$).

(E)-Ethyl 3-(4-aminophenyl)-2-butenoate (19b)

Compound 19a (929 mg), iron powder (1.97 g), and ammonium chloride (436 mg) were added to a mixed solution of tetrahydrofuran (4 ml), methanol (4 ml), and water (4 ml). The obtained mixture was stirred at 70° C. for 3.5 hours. The mixture was allowed to cool and then filtered. The filtrate was separated with ethyl acetate and water. The organic layer was sequentially washed twice with water and once with a saturated sodium chloride solution, and then dried over anhydrous sodium sulfate. The solvent was distilled off, and the residue was purified by column chromatography (17%-33% ethyl acetate/n-hexane) to obtain Compound 19b (757 mg, 96%) as an orange solid. $^1$H-NMR (CDCl$_3$) δ7.35 (2H, d, J=8.7 Hz), 6.65 (2H, d, J=8.7 Hz), 6.09 (1H, s), 4.19 (2H, q, J=7.1 Hz), 3.85 (2H, brs), 2.54 (3H, s), 1.30 (3H, t, J=7.1 Hz).

(E)-Ethyl 3-[4-[[3,5-bis(trimethylsilyl)benzoyl]amino]phenyl]-2-butenoate (19c)

Compound 19b (722 mg), EDC (878 mg), HOBt (619 mg), and 4-dimethylaminopyridine (560 mg) were added to a DMF (10 ml) solution of BTMB (1.22 g) in a nitrogen atmosphere, and the mixture was stirred at room temperature for 13 hours. The mixture was separated with water and a mixed solution of ethyl acetate and toluene. The organic layer was washed three times with water and once with a saturated sodium chloride solution, and then dried over anhydrous sodium sulfate. The solvent was distilled off, and the residue was suspended in petroleum ether and stirred. As a result, Compound 19c (1.02 g, 64%) was obtained as an opalescent solid.

$^1$H-NMR (CDCl$_3$) δ7.94 (2H, s), 7.83 (2H, s), 7.69 (2H, J=8.1 Hz), 7.53 (2H, d, J=8.1 Hz), 6.16 (1H, s), 4.22 (2H, q, J=7.0 Hz), 2.59 (3H, s), 1.32 (3H, t, J=7.0 Hz), 0.32 (18H, s); FAB-LRMS (negative) m/z 438 (M-H)$^-$.

(E)-3-[4-[[3,5-Bis(trimethylsilyl)benzenecarbothioyl]amino]phenyl]-2-butenoic acid (19)

Lawesson's reagent (134 mg) was added to a toluene (5 ml) solution of Compound 19c (300 mg), and the obtained mixture was stirred while refluxing under heating for 20 minutes. After the mixture was allowed to cool, the solvent was distilled off. The obtained residue was purified by column chromatography (6.25% ethyl acetate/n-hexane). Fractions containing the ester body of Compound 19 were collected and concentrated to dryness. As a result, 246 mg of yellow solid was obtained. The obtained yellow solid was, without further purification, dissolved in ethanol (10 ml), and a 2N sodium hydroxide aqueous solution (2.62 ml) was added thereto in a nitrogen atmosphere. The obtained mixture was stirred under heating at 70° C. for 2 hours. After the reaction was over, the mixture was allowed to cool. A 2N hydrochloric acid aqueous solution was added thereto, and the mixture was separated with ethyl acetate and water. The organic layer was washed once with water and once with a saturated sodium chloride solution, and then dried over anhydrous sodium sulfate. The solvent was distilled off, and as a result, Compound 19 (112 mg, 48%) was obtained as a yellow solid.

$^1$H-NMR (DMSO-d$_6$) δ7.92 (2H, d, J=8.6 Hz), 7.86 (2H, s), 7.77 (1H, s), 7.65 (2H, d, J=8.6 Hz), 6.17 (1H, s), 2.51 (3H, s), 0.33 (18H, s).

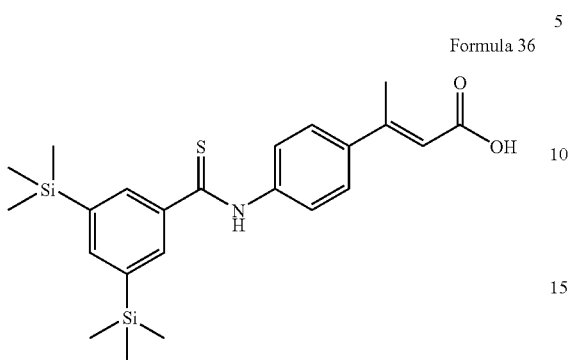

Formula 36

Example 20

Ethyl 3-[4-[[3,5-bis(trimethylsilyl)benzoyl]amino]phenyl]propanoate (20a)

Compound 17a (150 mg) was dissolved in methanol (35 ml) and ethyl acetate (35 ml). The obtained mixture was stirred for 30 minutes in a hydrogen atmosphere. After the reaction was over, the obtained reaction mixture was filtered through Cerite, and then washed with methanol. The solvent was distilled off from the filtrate, and the obtained residue was dried. Thus, Compound 20a (150 mg, quant.) was obtained as a white solid.

$^1$H-NMR (CDCl$_3$) δ7.93 (2H, s), 7.81 (1H, s), 7.71 (1H, s), 7.57 (2H, d, J=8.3 Hz), 7.22 (2H, d, J=8.3 Hz), 4.13 (2H, q, J=7.1 Hz), 2.97-2.93 (2H, m), 2.64-2.60 (2H, m), 1.25 (3H, t, J=7.1 Hz), 0.32 (18H, s).

3-[4-[[3,5-Bis(trimethylsilyl)benzenecarbothioyl]amino]phenyl]propanoic acid (20)

Lawesson's reagent (90 mg) was added to a toluene (5 ml) solution of Compound 20a (140 mg). The obtained mixture was stirred at 100° C. in a nitrogen atmosphere for 1 hour. After the reaction was over, the reaction mixture was allowed to cool, and concentrated. The obtained residue was purified by column chromatography (5% ethyl acetate/n-hexane). Fractions containing the ester body of Compound 4 were collected, and concentrated to dryness. As a result, 126 mg of yellow solid was obtained. The obtained yellow solid (90 mg) was, without further purification, dissolved in ethanol (1 ml). A 1N sodium hydroxide aqueous solution (1 ml) was added thereto in a nitrogen atmosphere. The obtained mixture was stirred under heating at 45° C. for 1 hour. After the reaction was over, the mixture was allowed to cool, and a 1N hydrochloric acid aqueous solution was added thereto. The mixture was separated with ethyl acetate and water. The organic layer was washed once with water and once with a saturated sodium chloride solution, and then dried over anhydrous sodium sulfate. The solvent was distilled off, and as a result, Compound 20 (54 mg, 64%) was obtained as an opalescent solid.

$^1$H-NMR (CDCl$_3$) δ7.92 (2H, s), 7.81 (1H, s), 7.71 (2H, d, J=8.3 Hz), 7.29 (2H, d, J=8.3 Hz), 3.01-2.96 (2H, m), 2.72-2.68 (2H, m), 0.31 (18H, s).

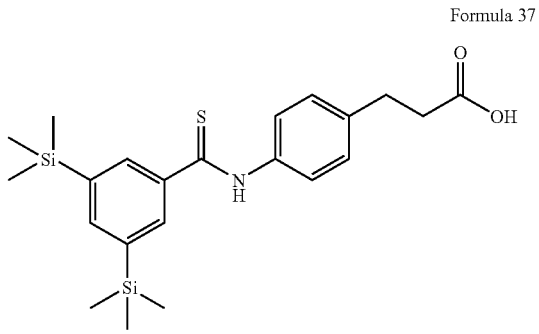

Formula 37

Pharmacological Test Example 1

Evaluation of RARα Selective Transcription-Activating Activity

Figure 2:
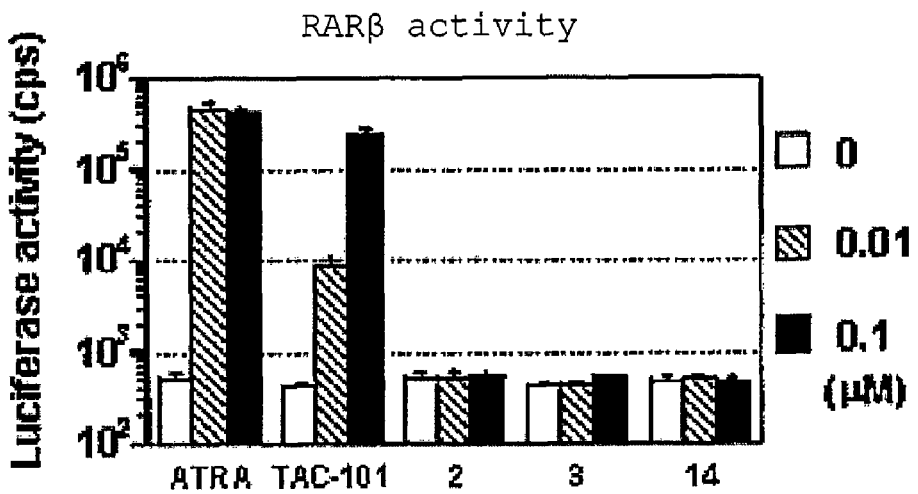
FIG. 2 is a graph showing the RARβ selective transcription-activating activity.
Figure 3:
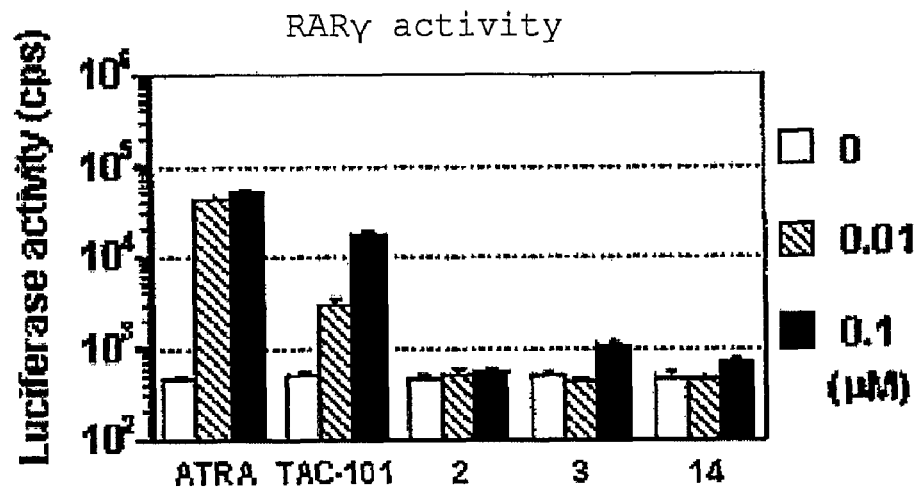
FIG. 3 is a graph showing the RARγ selective transcription-activating activity.

Human hepatocellular carcinoma cell lines JHH-7 were plated into a 24-well culture plate at a cell density of 4×10$^4$ cells per well. After culturing overnight, chimeric protein expression plasmid, in which each RAR subtype ligand binding site and a DNA binding site of a different transcription factor GAL4 were fused, and GAL4 reporter plasmid were introduced into the cells using FuGENE 6 (Roche Diagnostics). The cells were further cultured for 5 hours, and the compound of the present invention and the reference compounds, i.e., All-trans retinoic acid (hereinafter referred to as "ATRA") and TAC-101, were added thereto. After the cells were further cultured for 24 hours, culture supernatants were removed and cell proteins were recovered using a cell-lysing solution. Luciferase substrate (Promega) was added to evaluate the RAR selective activating activity using luciferase activity values as an index of the transcriptional-activating activity. This test is a test system that can evaluate RAR subtype selectivity without the influence of the endogenous RAR amount. The test results are shown in FIGS. 1 to 3. As is clear from FIG. 1, the transcription-activating activity against the RARα of the compounds of the invention was equivalent to that of the reference compounds. In contrast, as is clear from FIGS. 2 and 3, the transcription-activating activity against the RARβ and RARγ of the compounds of the invention was significantly lower than that of the reference compounds. These test results demonstrate that the compounds of the present invention had superior RARα selective activating activity to the reference compounds.

Pharmacological Test Example 2

Antitumor Effect of Compound of the Present Invention in JHH-7 (Human Hepatocellular Carcinoma Cell Lines) Orthotopic Liver Transplantation Model RARα high expression cells, i.e., human hepatocellular carcinoma cell lines JHH-7, were implanted in the outside left lobe of the liver of male nude mice (BALB/cA Jcl-nu; CLEA Japan, Inc.) under Nembutal anesthesia in an amount of 1×10$^6$ cells (0.02 ml) per mouse. On the 11th to 14th day after implantation, the mice were divided into groups, each consisting of seven mice. The compounds of the present invention and the reference compound TAC-101 were suspended in 0.5% HPMC and 1.6 mg/ml solution was orally administered to the mice at a liquid dose of 10 ml/kg, namely, at a dose of 16 mg/kg, once per day for 14 days. On the 15th day after the start of administration, the mice were exsanguinated to death under ether anesthesia. Tumors formed in the outside left lobe of the liver were extracted, and the tumor weight was measured to assess the antitumor effect. The antitumor effect was evaluated by calculating the tumor growth rate (%) using the following equation. The antitumor effect of each compound was analyzed by Student's test and statistical significance was determined.

Tumor growth rate(%)=$T/C\times 100$

T: Average tumor weight in the groups administered with the test compounds

C: Average tumor weight in the groups not administered with test compounds

The results are shown in FIG. 1.

TABLE 1

Table 1. Tumor growth rate (%)

| Compound | Tumor Growth Rate (%) |
| --- | --- |
| Control | 100 |
| 2 | 21 |
| 3 | 25 |
| 6 | 31 |
| 11 | 36 |
| TAC-101 | 52 |

As shown in Table 1, the tumor growth rate in the TAC-101-administered group was 52% in the orthotopic liver transplantation model. The tumor growth was suppressed by half in the Control group. This effect was statistically significant. On the other hand, the tumor growth in the groups administered with the compounds of the present invention was suppressed more remarkably as compared to the Control group. The therapeutic effect was clearly superior to TAC-101. These test results indicate that the compounds of the present invention have an even stronger antitumor effect than the existing RARα selective agonist.

Pharmacological Test Example 3

Figure 4:
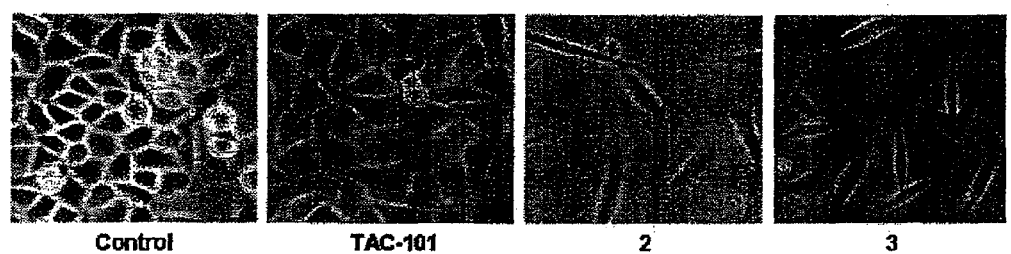
FIG. 4 is a micrograph showing the differentiation-inducing activity against prostate cancer cells.
Figure 5:
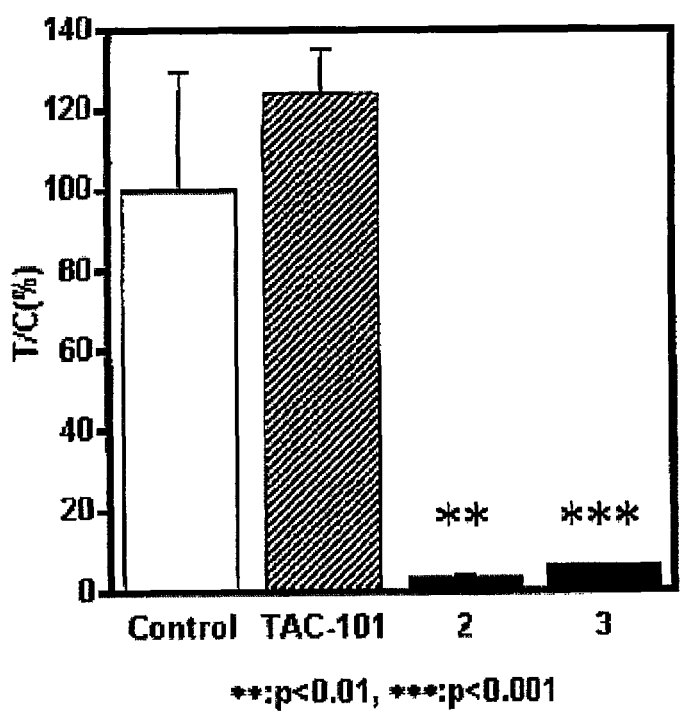
FIG. 5 is a graph showing the growth inhibitory effect on prostate cancer cells.

Growth Inhibitory Effect of Compound of the Present Invention on Prostate Cancer Cells Human prostatic carcinoma cell lines TSU-Pr1 prepared in RPMI1640 culture medium containing 2% fetal bovine serum were plated into a 24-well culture plate at a cell density of $3\times 10^3$ cells per well. The next day, IGF-I (10 ng/ml) was added as a growth factor, and the cells were treated with Compounds 2 and 3 of the present invention and the reference compound TAC-101 each in an amount of 10 μM. Change in cell shape after three days was observed. Moreover, on the 7th day after culturing, the cells were fixed with 25% glutaraldehyde solution. Cytostatic activity was determined by the crystal violet staining method, and the statistical significance of the cytostatic activity was analyzed by Student's test. FIG. 4 shows micrographs that illustrate differentiation-inducing activity on prostate cancer cells. In the Control group that was not treated with medicine, a cobblestone-like shape and vigorous cell division were observed. Such cell shape is characteristic of epithelioid cancer cells. In the TAC-101-treated group, although cell division images tended to decrease, no significant change was recognized in the shape. On the other hand, when the cells were treated with Compounds 2 or 3 of the invention, a dramatic change was recognized in the shape of neuroid cells. FIG. 5 shows the growth inhibitory effect on the 5th day after medicine treatment. In the groups treated with Compounds 2 and 3, which exhibited shape change, a dramatic cytostatic effect was recognized on the 7th day after culturing. More specifically, it was shown that the compounds of the present invention induced physiological changes, such as cell differentiation, even on cancer cells that did not exhibit sensitivity to the reference compound, thereby exerting a cancer cell growth inhibitory effect.

Pharmacological Test Example 4

Cancer Malignancy-Reducing Effect

Human prostatic carcinoma cell lines TSU-Pr1 were treated with Compound 3 of the present invention and the reference compound TAC-101 for 72 hours. The cells were subcutaneously implanted into male nude mice (BALB/cA Jcl-nu; CLEA Japan, Inc.) at six sites in total per mouse. On the 26th day after implantation, the rate of subcutaneous tumor formation was observed and the effect of reducing cancer malignancy was evaluated. Statistical significance was analyzed by Wilcoxon test.

TABLE 2

Table 2. Malignancy-reducing effect (reduction in tumorigenicity)
Malignancy-reducing effect (reduction in tumorigenicity)

| Compound | Tumor Formation | Graft Survival (%) | Wilcoxon Test |
| --- | --- | --- | --- |
| Control | 6/6 | 100 | — |
| TAC-101 | 4/6 | 67 | 0.145 |
| 3 | 1/6 | 17 | <0.001 |

According to Table 2, subcutaneous tumorigenesis was recognized in all six implantation sites in the Control group not treated with medicine, and the graft survival was 100%. In the TAC-101-treated group, although the graft survival was 67%, there was no significant difference from the Control group. On the other hand, in the Compound 3-treated group, the graft survival was 17%, and there was significant difference from the Control group. In addition, one survival example in the Compound 3-treated group exhibited a rudimentary tumor. This suggests that treatment with the compound of the present invention reduced the cancer malignancy, resulting in loss of tumorigenicity.

Pharmacological Test Example 5

Rat Toxicity Test

The compounds of the present invention and the reference compound TAC-101 were orally administered to male SD rats (CLEA Japan, Inc.) for 4 weeks. The dosage of each compound was 6 mg/kg or 24 mg/kg per rat. Differences in toxic symptoms were compared and studied.

TABLE 3

Table 3. Toxicity findings showing differences
Differences in Toxicity Symptom in
Rat Orally Administered for 4 Weeks

|  | Alopecia Symptom | | Endocortical Proliferation | |
| --- | --- | --- | --- | --- |
|  | 6 mg/kg | 24 mg/kg | 6 mg/kg | 24 mg/kg |
| TAC-101 | + | + | − | + |
| 2 | − | − | − | − |
| 3 | − | − | − | − |
| 14 | − | − | − | − |

According to Table 3, in the TAC-101-administered group, hair symptoms, which serve as a dermal toxicity index, were recognized in rats administered with 6 mg/kg of the compound, and endocortical proliferation, which serves as a bone toxicity index, was recognized in rats administered with 24 mg/kg of the compound. On the other hand, in the groups administered with Compounds 2, 3, and 14 of the present invention, these symptoms were not observed, even in rats administered with 24 mg/kg of the compound. In other words, these test results revealed that the compounds of the present invention reduced dermal toxicity as compared to the reference compound.

As previously described, dermal toxicity and bone toxicity caused by retinoid reportedly arise from RARγ. Due to the decline in RARγ agonist activity, toxic symptoms in the skin, etc. turned out to be remarkably reduced.

Formulation Example 1

Tablets

TABLE 4

| Compound (1) | 50 mg |
| --- | --- |
| Corn starch | 50 mg |
| Microcrystalline cellulose | 50 mg |
| Hydroxypropyl cellulose | 15 mg |
| Lactose | 47 mg |
| Talc | 2 mg |
| Magnesium stearate | 2 mg |
| Ethyl cellulose | 30 mg |
| Unsaturated glyceride | 2 mg |
| Titanium dioxide | 2 mg |

According to the above formulation, tablets each weighing 250 mg were prepared by a standard method.

Formulation Example 2

Granules

TABLE 5

| Compound (2) | 300 mg |
| --- | --- |
| Lactose | 540 mg |
| Corn starch | 100 mg |
| Hydroxypropyl cellulose | 50 mg |
| Talc | 10 mg |

According to the above formulation, granules were prepared by a standard method, each dose weighing 1000 mg.

Formulation Example 3

Capsules

TABLE 6

| Compound (3) | 100 mg |
| --- | --- |
| Lactose | 30 mg |
| Corn starch | 50 mg |
| Microcrystalline cellulose | 10 mg |
| Magnesium stearate | 3 mg |

According to the above formulation, capsules each weighing 193 mg were prepared by a standard method.

Formulation Example 4

Injection

TABLE 7

| Compound (4) | 100 mg |
| --- | --- |
| Sodium chloride | 3.5 mg |
| Distilled water for injection | Proper quantity (2 ml per ample) |

According to the above formulation, an injection was prepared by a standard method.

Formulation Example 5

Syrup

TABLE 8

| Compound (6) | 200 mg |
| --- | --- |
| Purified sucrose | 60 g |
| Ethyl p-hydroxybenzoate | 5 mg |
| Butyl p-hydroxybenzoate | 5 mg |
| Flavoring | Proper quantity |
| Colorant | Proper quantity |
| Purified water | Proper quantity |

According to the above formulation, a syrup was prepared by a standard method.

Formulation Example 6

Suppository

TABLE 9

| Compound (8) | 300 mg |
| --- | --- |
| Witepsol W-35*[1] | 1400 mg |

*[1]Trade Mark; mixture of mono-, di-, and triglycerides of saturated fatty acid from lauric acid to stearic acid; product of Dynamit Nobel AG According to the above formulation, a suppository was prepared by a standard method.

The invention claimed is:

1. A bis(trimethylsilyl)phenyl compound represented by Formula (I):

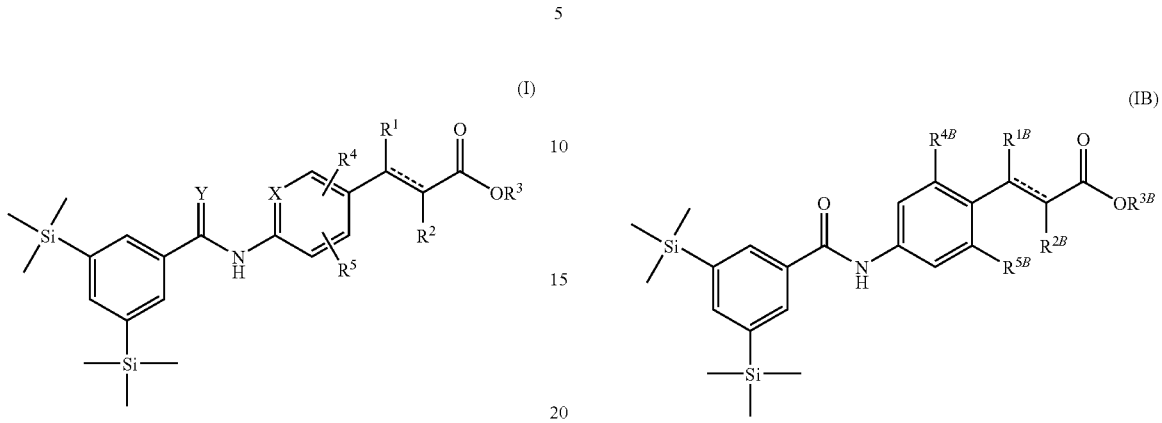

wherein X is N or CH;
Y is O or S;
$R^1$, $R^2$, and $R^3$ are the same or different and are hydrogen or lower alkyl;
$R^4$ and $R^5$ are the same or different and are hydrogen, lower alkyl, or halogen; and
a bond between a carbon atom to which $R^1$ is attached and a carbon atom to which $R^2$ is attached is a single bond or a double bond;
or a salt thereof.

2. A bis(trimethylsilyl)phenyl compound according to claim 1 represented by Formula (IA):

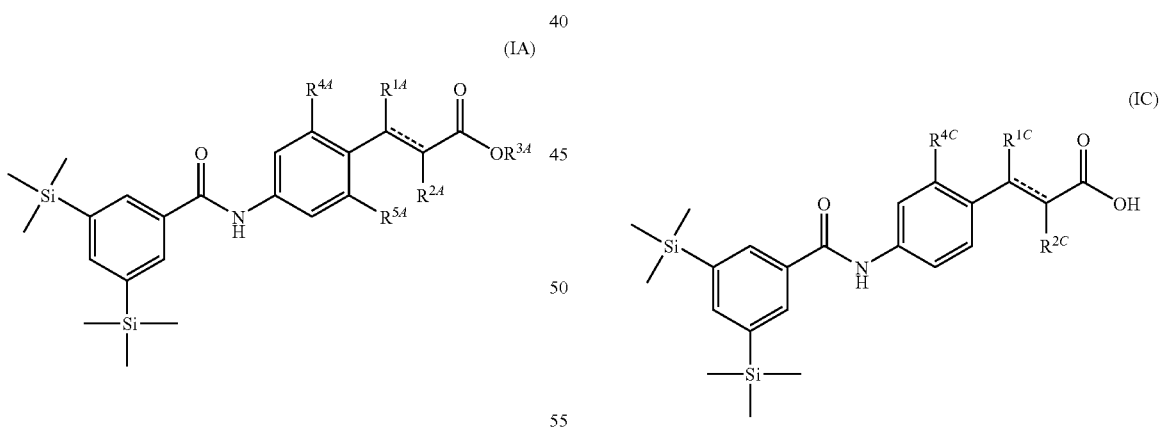

wherein one of $R^{1A}$ and $R^{2A}$ is hydrogen and the other is lower alkyl, or both $R^{1A}$ and $R^{2A}$ are hydrogen;
$R^{3A}$ is hydrogen, methyl, or ethyl;
$R^{4A}$ is hydrogen, lower alkyl, or halogen;
$R^{5A}$ is hydrogen or halogen; and
a bond between a carbon atom to which $R^{1A}$ is attached and a carbon atom to which $R^{2A}$ is attached is a single bond or a double bond;
or a salt thereof.

3. A bis(trimethylsilyl)phenyl compound according to claim 1 represented by Formula (IB):

wherein one of $R^{1B}$ and $R^{2B}$ is hydrogen and the other is methyl, or both $R^{1B}$ and $R^{2B}$ are hydrogen;
$R^{3B}$ is hydrogen or methyl;
$R^{4B}$ is hydrogen, methyl, fluorine, or chlorine;
$R^{5B}$ is hydrogen or fluorine; and
a bond between a carbon atom to which $R^{1B}$ is attached and a carbon atom to which $R^{2B}$ is attached is a single bond or a double bond;
or a salt thereof.

4. A bis(trimethylsilyl)phenyl compound according to claim 1 represented by Formula (IC):

wherein one of $R^{1C}$ and $R^{2C}$ is hydrogen and the other is methyl, or both $R^{1C}$ and $R^{2C}$ are hydrogen;
$R^{4C}$ is hydrogen, methyl, fluorine, or chlorine; and
a bond between a carbon atom to which $R^{1C}$ is attached and a carbon atom to which $R^{2C}$ is attached is a double bond;
or a salt thereof.

5. A bis(trimethylsilyl)phenyl compound according to claim 1 represented by Formula (ID):

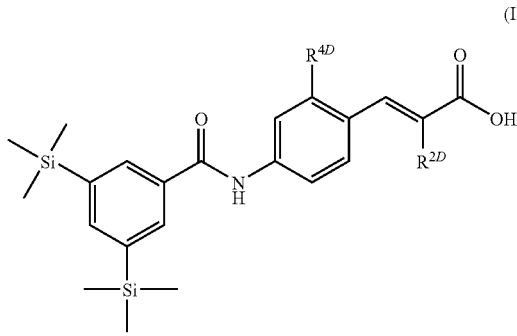

(ID)

wherein $R^{2D}$ is methyl or hydrogen; and
$R^{4D}$ is hydrogen or fluorine;
or a salt thereof.

6. A bis(trimethylsilyl)phenyl compound according to claim 1 or a salt thereof, wherein in Formula (I),
X is N or CH;
Y is S;
$R^1$ is lower alkyl or hydrogen;
$R^2$ is hydrogen;
$R^3$ is hydrogen, methyl, or ethyl;
both $R^4$ and $R^5$ are hydrogen; and
a bond between a carbon atom to which $R^1$ is attached and a carbon atom to which $R^2$ is attached is a single bond or a double bond.

7. A bis(trimethylsilyl)phenyl compound according to claim 1 selected from the group consisting of:
4-[[3,5-bis(trimethylsilyl)benzoyl]amino]-2-fluorocinnamic acid;
4-[[3,5-bis(trimethylsilyl)benzoyl]amino]cinnamic acid;
3-[4-[[3,5-bis(trimethylsilyl)benzoyl]amino]phenyl]propanoic acid;
(E)-3-[4-[[3,5-bis(trimethylsilyl)benzoyl]amino]phenyl]-2-butenoic acid; and
(E)-3-[4-[[3,5-bis(trimethylsilyl)benzoyl]amino]-2-fluorophenyl]-2-methylacrylic acid;
or a salt thereof.

8. A pharmaceutical composition comprising, as an active ingredient, a bis(trimethylsilyl)phenyl compound or a salt thereof according to claim 1.

9. An RARα agonist comprising, as an active ingredient, a bis(trimethylsilyl)phenyl compound or a salt thereof according to claim 1.

10. An antitumor agent comprising, as an active ingredient, a bis(trimethylsilyl)phenyl compound or a salt thereof according to claim 1.

11. A method for treating a disease that is effectively treated by an increase in RARα activity, the method comprising administering to a patient an effective amount of a bis(trimethylsilyl)phenyl compound or a salt thereof according to claim 1.

* * * * *